US012630573B2

(12) United States Patent
Fahrni et al.

(10) Patent No.: US 12,630,573 B2
(45) Date of Patent: May 19, 2026

(54) HIGH-AFFINITY CU(I) LIGANDS AND METHODS OF USE THEREOF

(71) Applicant: GEORGIA TECH RESEARCH CORPORATION, Atlanta, GA (US)

(72) Inventors: Christoph J. Fahrni, Atlanta, GA (US); M. Thomas Morgan, Brookhaven, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1175 days.

(21) Appl. No.: 17/598,929

(22) PCT Filed: Mar. 30, 2020

(86) PCT No.: PCT/US2020/025771
§ 371 (c)(1),
(2) Date: Sep. 28, 2021

(87) PCT Pub. No.: WO2020/198742
PCT Pub. Date: Oct. 1, 2020

(65) Prior Publication Data

US 2022/0169669 A1 Jun. 2, 2022

Related U.S. Application Data

(60) Provisional application No. 62/825,193, filed on Mar. 28, 2019.

(51) Int. Cl.
*C07F 9/6558* (2006.01)
*A61K 33/34* (2006.01)
(Continued)

(52) U.S. Cl.
CPC .......... *C07F 9/65586* (2013.01); *A61K 33/34* (2013.01); *A61K 45/06* (2013.01);
(Continued)

(58) Field of Classification Search
None
See application file for complete search history.

(56) References Cited

U.S. PATENT DOCUMENTS

2013/0172270 A1* 7/2013 Lam .......................... C07K 14/78 435/375
2020/0326597 A1* 10/2020 Rogojina .............. G02F 1/1303

FOREIGN PATENT DOCUMENTS

WO WO-9630056 A1 * 10/1996 .......... A61K 51/0478
WO 2020/198742 A1 10/2020

OTHER PUBLICATIONS

Kaim (Organophosphorous Redox Systems, 1983, Journal of Organic Chemistry, 48(23):4206-4209) (Year: 1983).*
(Continued)

*Primary Examiner* — Michael G. Hartley
*Assistant Examiner* — Kaila A Craig
(74) *Attorney, Agent, or Firm* — Smith Gambrell & Russell LLP

(57) ABSTRACT

Several dimethylphosphine sulfide- and phosphine-containing compounds have been discovered that chelate copper(I) with high affinity. In certain embodiments, the compounds can be used to quantify copper(I) in complex biological systems. In another embodiment, the compounds can be used for the treatment of copper(I)-related illnesses and conditions. In still other embodiments, the compounds are ratiometric probes.

8 Claims, 10 Drawing Sheets

1A

PSP-1

1B

PSP-2

1C

1D phenPS

1E naphPS

(51) Int. Cl.
*A61K 45/06* (2006.01)
*C07F 9/40* (2006.01)
*G01N 33/84* (2006.01)

(52) U.S. Cl.
CPC .......... *C07F 9/4093* (2013.01); *G01N 33/84* (2013.01); *G01N 2800/2821* (2013.01); *G01N 2800/2835* (2013.01); *G01N 2800/7028* (2013.01)

(56) References Cited

OTHER PUBLICATIONS

Trippier (Synthetic Strategies for the Biotinylation of Bioactive Small Molecules, Jan. 28, 2013, ChemMedChem, vol. 8, Issue 2) (Year: 2013).*

King (Poly(tertiary phosphines and arsines). X. The Syntheses of Methylated Poly(tertiary phosphines), Jan. 1, 1975, Journal of the American Chemical Society, 97(1):53-60) (Year: 1975).*

Sato (Bridging Adhesion of a Protein onto an Inorganic Surface Using Self Assembled Dual-Functionalized Spheres, Jul. 19, 2015, Journal of the American Chemical Society, 137:12890-12896) (Year: 2015).*

Ashwell et al., "Carbohydrate-Specific Receptors of the Liver", Ann. Rev. Biochem., vol. 51, 1982, 531-534.

Badarau et al., "Copper Trafficking Mechanism of CXXC-Containing Domains: Insight from the pH-Dependence of Their Cu(I) Affinities", Journal of the American Chemical Society, vol. 133, No. 9, 2011, pp. 2983-2988.

Bagchi et al., "Robust Affinity Standards for Cu(I) Biochemistry", J. Am. Chem. Soc., vol. 135, No. 49, Dec. 11, 2013, pp. 18549-18559.

Cotruvo et al., "Synthetic fluorescent probes for studying copper in biological systems", Chemical Society Reviews, vol. 44, 2015, pp. 4400-4414.

Fahrni et al., "Synthetic Fluorescent Probes for Monovalent Copper", Curr Opin Chem Biol., vol. 17, No. 4, 2013, pp. 656-662.

Grynkiewicz et al., "A New Generation of Ca2+ Indicatorsw ith Greatly Improved Fluorescence Properties", The Journal of Biological Chemistry, vol. 260, No. 6, Mar. 25, 1985, pp. 3440-3450.

Heuberger et al., "High-affinity Cu(I) chelator PSP-2 as potential anti-angiogenic agent", Scientific Reports, vol. 9, 2019, pp. 14055.

International Preliminary Report on Patentability received for PCT Patent Application No. PCT/US2020/025771, mailed on Oct. 7, 2021, 6 pages.

International Search Report and Written Opinion received for PCT Patent Application No. PCT/US2020/025771, mailed on Jun. 16, 2020, 6 pages.

Morgan et al., "Glutathione limits aquacopper(I) to sub-femtomolar concentrations through cooperative assembly of a tetranuclear cluster", J. Biol. Chem., vol. 292, No. 52, 2017, pp. 21558-21567.

Morgan et al., "Stabilization of Aliphatic Phosphines by Auxiliary Phosphine Sulfides Offers Zeptomolar Affinity and Unprecedented Selectivity for Probing Biological CuI", Angewandte chemie, international edition, vol. 57, No. 31, Jul. 26, 2018, pp. 9711-9715.

Shen et al., "What has fluorescent sensing told us about copper and brain malfunction?", Metallomics, vol. 7, No., 1, 2015, pp. 56-65.

Xiao et al., "Unification of the Copper(I) Binding Affinities of the Metallo-chaperones Atx1, Atox1, and Related Proteins", Journal of Biological Chemistry, vol. 286, No. 13, Apr. 1, 2011, pp. 11047-11055.

Chelation' in IUPAC Compendium of Chemical Terminology, 5th ed. International Union of Pure and Applied Chemistry; 2025. Online version 5.0.0, 2025. https://doi.org/10.1351/goldbook.C01012 IUPAC-chelation (C01012) https://doi.org.

J. J. R. Frausto da Silva, "The chelate effect redefined", Journal of Chemical Education, vol. 60, No. 5, May 1, 1983, 3 pages.

Martell, A. E., "The Chelate Effect", Mar. 11, 2025, 23 pages.

Nabatilan, A., et al., "Selective removal of copper from complex biological media with an agarose-immobilized high-affinity PSP ligand", JBIC Journal of Biological Inorganic Chemistry, vol. 29, 2024, pp. 531-540.

Saeedifard, F., et al., "Preorganized PSP Ligands Yield Monomeric Cu(I) Complexes with Subzeptomolar Cu(I) Dissociation Constants", Inorg. Chem., vol. 58, 2019, pp. 13631-13638.

Bagchi, et al., "Robust Affinity Standards for Cu(I) Biochemistry." J. Am. Chem. Soc. 135:18549-18559 (2013).

Morgan, et al., "Stabilization of Aliphatic Phosphines by Auxiliary Phosphine Sulfides Offers Zeptomolar Affinity and Unprecedented Selectivity for Probing Biological CuI." Angew. Chem. Int. Ed. Engl. 57(31):9711-9715 (2018).

Burns, et al., "Selective Reduction of Disulfides by Tris(2-carboxyethyl)phosphine." J. Org. Chem. 56:2648-2650 (1991).

* cited by examiner 1A 1B 1C 1D 1E
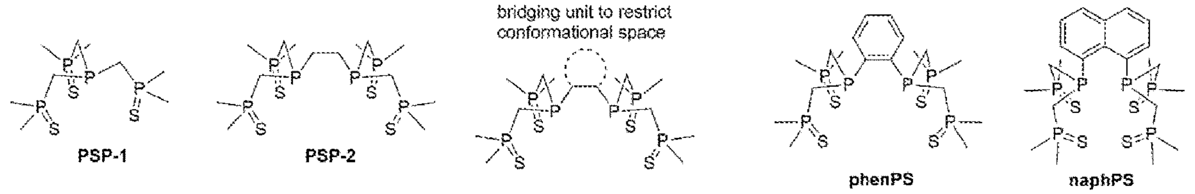
PSP-1 PSP-2 phenPS naphPS
FIGS. 1A-1E
2A 2B 2C 2D
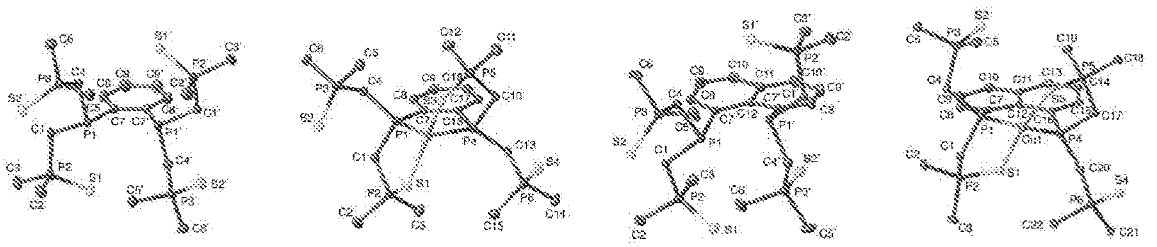
FIGS. 2A-2D
3A 3B 3C 3D
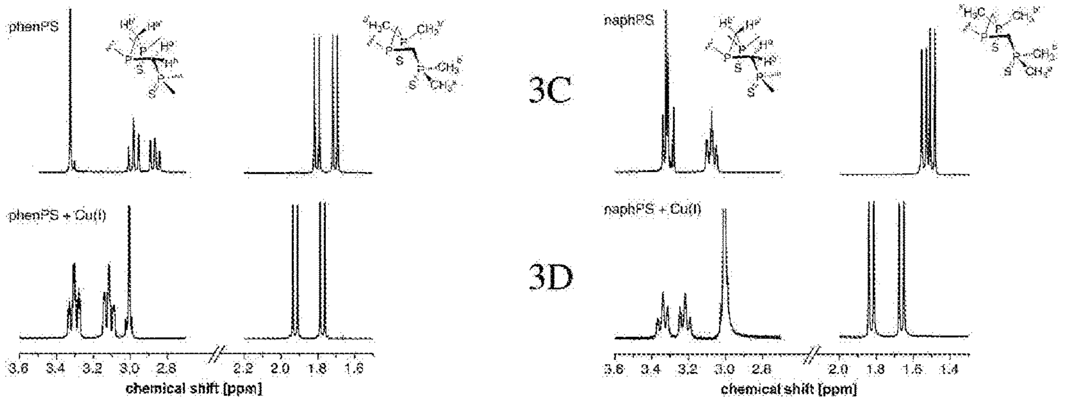
FIGS. 3A-D

FIGS. 5A-5P
5A
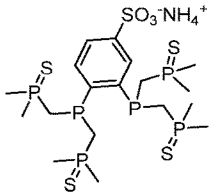
5B
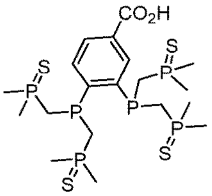
5C
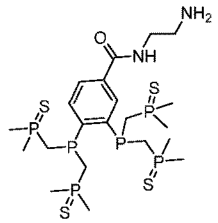
5D
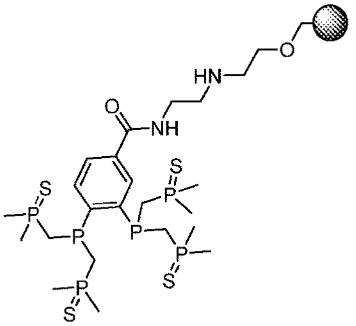
5E
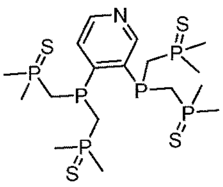
5F
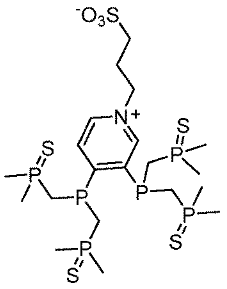
5G
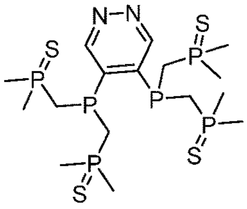
5H
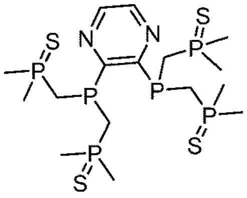
5I
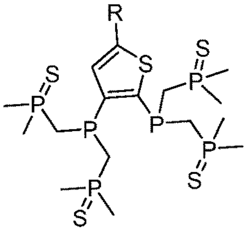
5J
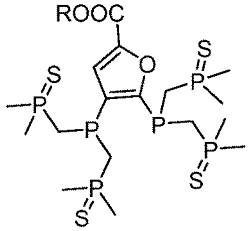
5K
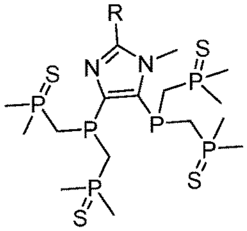
5L
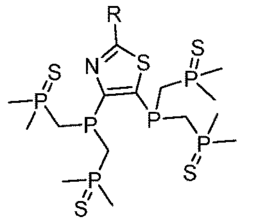
5M
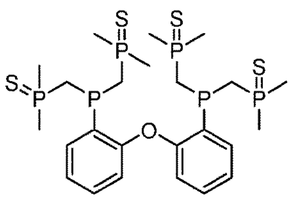
5N
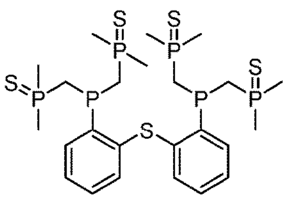
5O
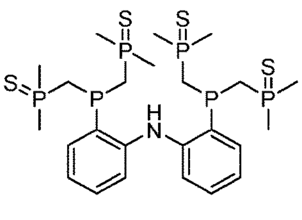
5P
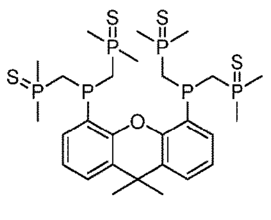

FIGS. 5Q-5AB
5Q
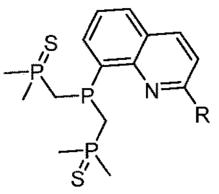
5R
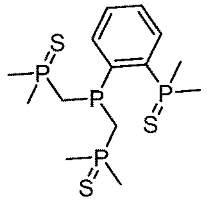
5S
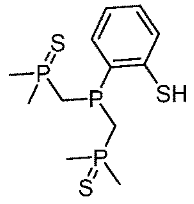
5T
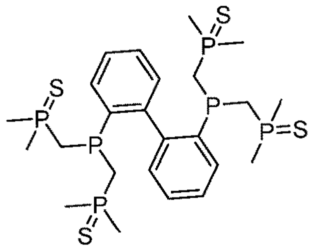
5U
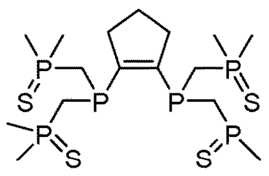
5V
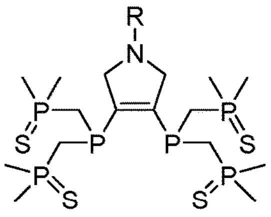
5W
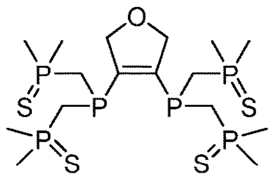
5X
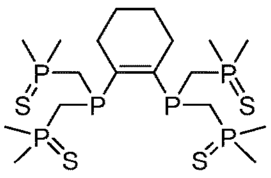
5Y
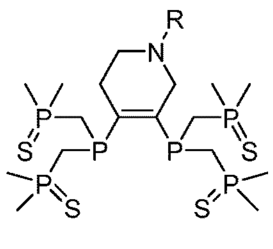
5Z
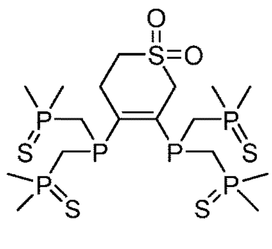
5AA
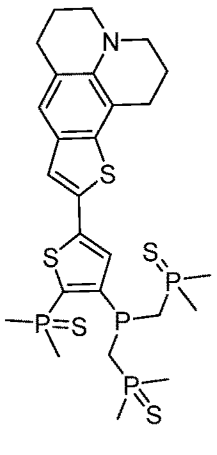
5AB
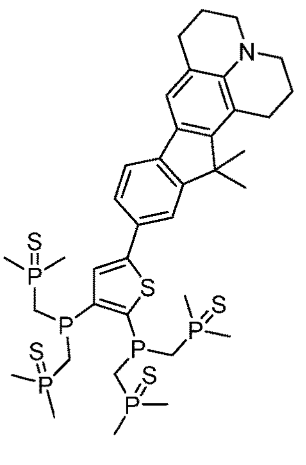

FIGS. 5AC-5AI
5AC
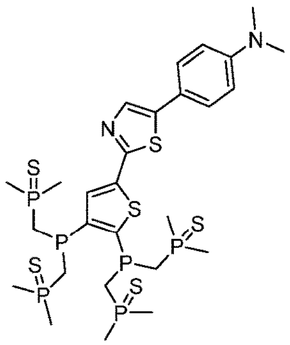
5AD
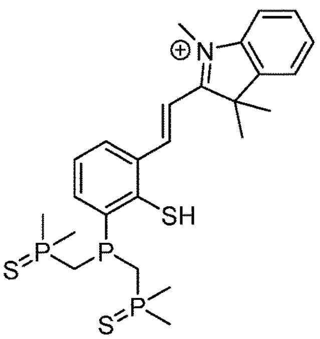
5AE
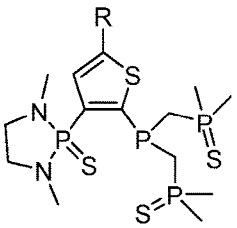
5AF
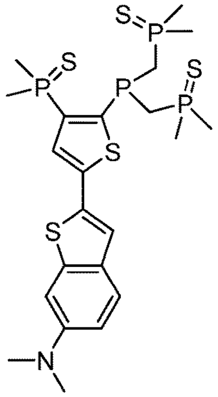
5AG
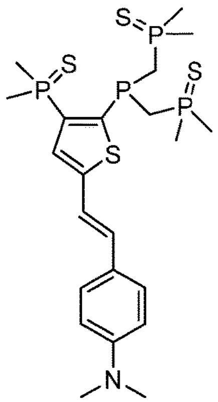
5AH
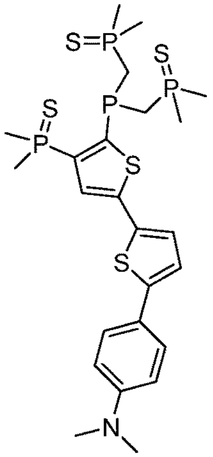
5AI
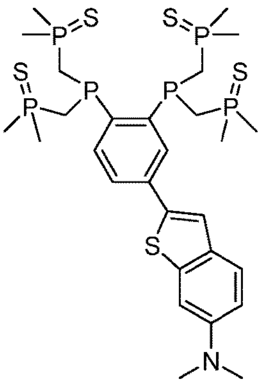

HIGH-AFFINITY CU(I) LIGANDS AND METHODS OF USE THEREOF

CROSS REFERENCE TO RELATED APPLICATIONS

This application is a national stage application, filed under 35 U.S.C. § 371, of International Patent Application No. PCT/US2020/025771 filed on Mar. 30, 2020, which claims benefit of and priority to U.S. Provisional Patent Application No. 62/825,193 filed on Mar. 28, 2019, which are incorporated herein by reference in their entirety.

STATEMENT REGARDING FEDERALLY SPONSORED RESEARCH

This invention was made with government support under grant No. R01GM067169 awarded by National Institutes of Health. The government has certain rights in the invention.

TECHNICAL FIELD OF THE INVENTION

The invention is generally directed to compositions and methods for chelating copper(I) in complex biological systems.

BACKGROUND OF THE INVENTION

Copper is an essential metal for most living matter. It plays a role in a variety of processes, including cellular respiration, defense against reactive oxygen species, electron transfer/substrate oxidation, pigmentation, antioxidant defense, biosynthesis of neurotransmitters, metabolism, and connective tissue maturation (Cotruvo, J. A. et al., *Chem. Soc. Rev.,* 44:4400 (2015)). Copper acts as an essential cofactor for many proteins including cytochrome c oxidase, ceruloplasmin, tyrosinase, Cu/Zn superoxide dismutases, dopamine β-hydroxylase, peptidylglycine α-amidating monooxygenase, lysyl oxidase-like, and copper amine oxidases (Cotruvo, J. A. et al., *Chem. Soc. Rev.,* 44,4400 (2015)).

As such, defects in copper homeostasis and trafficking can lead to a variety of disease states. Menkes and Wilson's disease are human genetic disorders in which copper is dysregulated. Copper dysregulation is implicated in various neurodegenerative diseases such as Alzheimer's, Parkinson's, Huntington's, and prion diseases. Copper is also implicated in metabolic disorders such as obesity and diabetes. More recently, copper has been found to play a role in the regulation of cancers via oncogenic BRAF mutations.

Copper is typically stored and transported as copper(I) (Cu(I)). While free aquocopper(I) ions would be susceptible to oxidation by dioxygen, increasing evidence suggests that the exchangeable pool of cellular copper is stabilized by bioligands, which buffer cytosolic Cu(I) at attomolar levels or below (Badarau, A., et al., *J. Am. Chem. Soc.,* 133(9), 2983-2988; Morgan, M. T., et al., *J. Biol. Chem.,* 292(52), 21558-21567; Xiao, Z., et al., *J. Biol. Chem.,* 286, 11047-11055). Dissociation constants below 1 fM are challenging to realize with commonly employed synthetic Cu(I) chelators based on thioether donors (Cotruvo, J. A. et al., *Chem. Soc. Rev.,* 44,4400 (2015); Fahrni, C. J., et al., *Curr. Opin. Chem. Biol.,* 17, 656-662 (2013); Shen, C., et al., *Metallomics,* 7(1), 56-65 (2015)). It was recently demonstrated that improved dissociation constants are attainable with aliphatic phosphine-based ligands containing auxiliary phosphine sulfide moieties (Morgan, M. T., et al., *Angew. Chem. Int. Ed.*

*Engl.,* 57, 9711-9715, (2018)). The latter not only participate in Cu(I) coordination but also exert an electron withdrawing effect on the phosphine sites, stabilizing the free ligand against protonation and oxidation. These first-generation phosphine sulfide-stabilized phosphines, typified by PSP-1 and PSP-2 (FIG. 1A and FIG. 1), maintain strong Cu(I) coordinating ability despite dramatically reduced basicity compared to typical aliphatic phosphines. With a 1:1 Cu(I) complex stability constant of log K=20.0 ($K_d$=10 zM), PSP-2 offers an unprecedented Cu(I) affinity among synthetic ligands and is unaffected by Mn(II), Fe(II), or Zn(II) even at millimolar concentrations (Morgan, M. T., et al., *Angew. Chem. Int. Ed. Engl.,* 57, 9711-9715, (2018)). PSP-2 was shown to significantly reduce cellular Cu(I) levels and exhibit significant anti-angiogenic effects, as well as exhibited anti-tumorigenic activity (Hueberger, D. M., et al., *Sci. Reports,* 9, 14055 (2019)). The Cu(I) complexes of both PSP-1 and PSP-2, however, engage in additional dimerization equilibria, and the highest-affinity ligand PSP-2 exhibits limited redox stability in solution.

Therefore, it is an object of this invention to provide compositions and methods for the chelating of copper(I).

It is another object of this invention to provide compositions and methods for treating copper-related illnesses.

It is still another object of the invention to provide methods and systems for detecting and quantifying copper, for example in complex biological environments.

SUMMARY OF THE INVENTION

Copper chelators and methods of their use are provided. One embodiment provides a compound according to Formula I:

(Formula I)

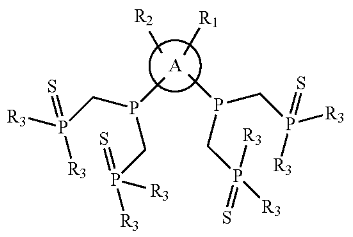

wherein:

A is any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, ferrocene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

$R_1$ and $R_2$ are independently selected from —H, halogen, —$NH_2$, —$CONH_2$, —$NO_2$, —$CH_3$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), $SO_2N$($C_1$-$C_{30}$ alkyl)($C_1$-$C_{30}$ alkyl), —OH, —SH, —COO($C_1$-$C_{30}$ alkyl), $C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$;

$R_3$ is selected from —$C_1$-$C_{30}$ alkyl, —NH($C_1$-$C_{30}$ alkyl), —N($C_1$-$C_{30}$ alkyl)$_2$, —O($C_1$-$C_{30}$ alkyl)OH, or —S($C_1$-$C_{30}$ alkyl)SH; and $R_4$ is selected from halogen, —$NO_2$, —$NH_2$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

Another embodiment provides a compound according to Formula II:

(Formula II)

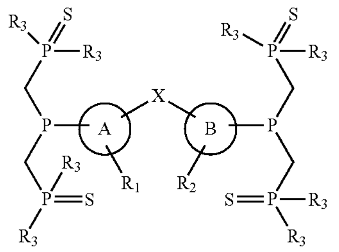

wherein:

A and B are independently any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, ferrocene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

X is selected from —O—, —S—, —N(H)—, —N(alkyl)-, —$C_1$-$C_{30}$ alkyl-, —($C_1$-$C_{30}$ alkyl)-O—($C_1$-$C_{30}$ alkyl)-, —($C_1$-$C_{30}$ alkyl)-N—($C_1$-$C_{30}$ alkyl)-, or —($C_1$-$C_{30}$ alkyl)-S—($C_1$-$C_{30}$ alkyl)-; $R_1$ and $R_2$ are independently selected from —H, halogen, —$NH_2$, —$CONH_2$, —$NO_2$, —$CH_3$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), $SO_2$N($C_1$-$C_{30}$ alkyl)($C_1$-$C_{30}$ alkyl), —OH, —SH, —COO($C_1$-$C_{30}$ alkyl), $C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$; and $R_3$ is selected from —$C_1$-$C_{30}$ alkyl, —NH($C_1$-$C_{30}$ alkyl), —N($C_1$-$C_{30}$ alkyl)$_2$, —O($C_1$-$C_{30}$ alkyl)OH, or —S($C_1$-$C_{30}$ alkyl)SH; and $R_4$ is selected from halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

Another embodiment provides a compound according to Formula III:

(Formula III)

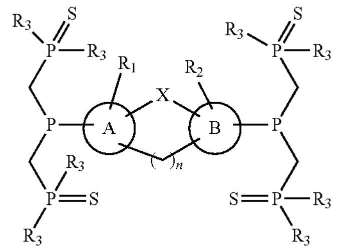

wherein:

A and B are independently any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

X is selected from —O—, —S—, —N(H)—, —N(alkyl)-, —$C_1$-$C_{30}$ alkyl-, —($C_1$-$C_{30}$ alkyl)-O—($C_1$-$C_{30}$ alkyl)-, —($C_1$-$C_{30}$ alkyl)-N—($C_1$-$C_{30}$ alkyl)-, or —($C_1$-$C_{30}$ alkyl)-S—($C_1$-$C_{30}$ alkyl)-;

$R_1$ and $R_2$ are independently selected from —H, -halogen, —$NH_2$, —$CONH_2$, —$NO_2$, —$CH_3$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), $SO_2$N($C_1$-$C_{30}$ alkyl)($C_1$-$C_{30}$ alkyl), —OH, —SH, —COO($C_1$-$C_{30}$ alkyl), —$C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$; and $R_3$ is selected from —$C_1$-$C_{30}$ alkyl, —NH($C_1$-$C_{30}$ alkyl), —N($C_1$-$C_{30}$ alkyl)$_2$, —O($C_1$-$C_{30}$ alkyl)OH, or —S($C_1$-$C_{30}$ alkyl)SH; and $R_4$ is selected from halogen, —$NO_2$, —$NH_2$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

n is selected from zero to five;

Another embodiment provides a compound according to Formula IV:

(Formula IV)

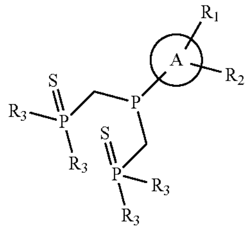

wherein:

A is any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, ferrocene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

$R_1$ is independently selected from —H, halogen, —$NH_2$, —$CONH_2$, —$NO_2$, —$CH_3$, —$SO_3H$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), $SO_2N$($C_1$-$C_{30}$ alkyl)($C_1$-$C_{30}$ alkyl), —OH, —SH, —COO($C_1$-$C_{30}$ alkyl), —COOH, $C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$;

$R_2$ is independently selected from —H, halogen, —$NH_2$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —OH, —SH, —C(S)SH, —C(O)SH, —COO($C_1$-$C_{30}$ alkyl), any aromatic system including but not limited to triazole, tetrazole, imidazole, pyrazole, pyridine, pyrimidine optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$, -(phosphanediylbis(methylene))bis(dimethylphosphine sulfide), -dimethylphosphine sulfide, —$P(R_5)_2$, —$P(S)(R_5)_2$, or —$P(O)(R_5)_2$;

$R_3$ is selected from —$C_1$-$C_{30}$ alkyl, —NH($C_1$-$C_{30}$ alkyl), —N($C_1$-$C_{30}$ $alkyl)_2$, —O($C_1$-$C_{30}$ alkyl)OH, or —S($C_1$-$C_{30}$ alkyl)SH; and $R_4$ is selected from halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2N$($C_1$-$C_{30}$ alkyl)($C_1$-$C_{30}$ alkyl), —OH, —SH, —COO($C_1$-$C_{30}$ alkyl), —COOH, or —$C_1$-$C_{30}$ alkyl; and $R_5$ is selected from —OH, —SH, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —$C_1$-$C_{30}$ alkyl which can be optionally substituted with $R_4$, any aromatic system optionally substituted with $R_4$, a carbocycle or heterocycle optionally substituted with $R_4$, or a polycyclic carbocycle or heterocycle optionally substituted with $R_4$;

or an enantiomer, polymorph or salt thereof.

Another embodiment provides for the compound according to Formula V:

(Formula V)

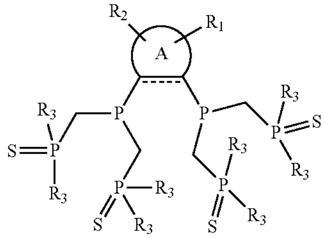

wherein:

A is any monocyclic or polycyclic saturated or unsaturated aliphatic or heteroaliphatic system including but not limited to azetidine, aziridine, cyclobutane, cyclobutene, cyclohexane, cyclohexene, cyclopropane, cylopropene, cyclopentene, cyclopentane, oxetane, norbornane, norbornene, piperidine, pyrrolidine, pyrimidine, tetrahydrofuran, thietane, thiolane, thiolane, thiolane-1-oxide, thiolane-1,1-dioxide; and $R_1$ and $R_2$ are independently selected from —H, -halogen, —O—($C_1$-$C_{30}$ alkyl), —NH—($C_1$-$C_{30}$ alkyl), —$SO_3H$, —COOH, —S—($C_1$-$C_{30}$ alkyl), —N($C_1$-$C_{30}$ alkyl)($C_1$-$C_{30}$ alkyl), —OH, —SH, —COO($C_1$-$C_{30}$ alkyl), —CON—($C_1$-$C_{30}$ alkyl)-N—($C_1$-$C_{30}$ alkyl)-OH, —$CONH_2$, —CON($C_1$-$C_{30}$ alkyl)($C_1$-$C_{30}$ alkyl), —$SO_2$($C_1$-$C_{30}$ alkyl), —$SO_2N$($C_1$-$C_{30}$ alkyl)($C_1$-$C_{30}$ alkyl), —$C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$, -1,3-dimethyl-1,3,2-diazaphospholidine 2-sulfide, (phosphanediylbis(methylene))bis(dimethylphosphine sulfide), or -dimethylphosphine sulfide;

$R_3$ is selected from —$C_1$-$C_{30}$ alkyl, —NH($C_1$-$C_{30}$ alkyl), —N($C_1$-$C_{30}$ $alkyl)_2$, —O($C_1$-$C_{30}$ alkyl)OH, or —S($C_1$-$C_{30}$ alkyl)SH;

$R_4$ is selected from halogen, —$NO_2$, —$NH_2$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2N$($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

Another embodiment provides for the compound according to Formula VI:

(Formula VI)

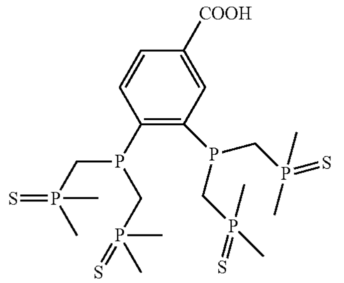

or an enantiomer, polymorph or salt thereof.

Still, another embodiment provides for the compound according to Formula VII:

(Formula VII)

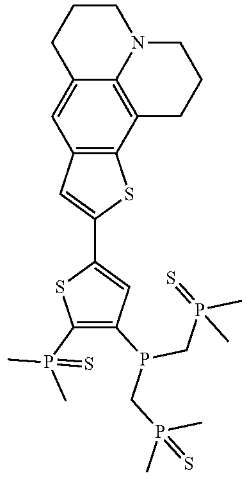

or an enantiomer, polymorph or salt thereof.

In some embodiments a compound of Formula I, II, III, IV, V, VI, or VII is conjugated to a protein, fluorophore, small molecules such as biotin or other biological ligands. This could be beneficial for targeting, imaging, and/or quantifying.

One embodiment provides a method of chelating copper using compositions containing a compound of Formula I, II, III, IV, V, VI, or VII or an enantiomer, polymorph or salt thereof by adding an effective amount of the compound to a solution containing copper. In one embodiment the copper that is chelated is copper(I). In another embodiment the source of the copper to be chelated is from copper(II). For example, copper(II) can be reduced in a sample by adding a reducing agent. Exemplary reducing agents include but are not limited to sodium ascorbate, glutathione, dihydrolipoic acid, hydroxylamine, dithiothreitol (DTT), triphenyl phosphine, mercaptoethanol, tris(2-carboxyethyl)phosphine (TCEP), 2,3-dimercaptopropanesulfonate (DMPS), 2-mercaptoethanesulfonate (MESNA), (2S)-2-amino-1,4-dimercaptobutane (DTBA), sodium ascorbate, and hydroxylamine. The copper chelating compounds can then chelate the copper(I) produced from the reduction of copper(II) in the sample. The sample can be a biological sample or an industrial sample.

Another embodiment provides a method of chelating and quantifying copper using compositions containing a compound of Formula I, II, III, IV, V, VI, or VII or an enantiomer, polymorph or salt thereof. The method includes steps of contacting the sample with one or more of the disclosed compounds to form a compound-copper complex, separating the complex from the sample, and quantifying the amount of complex present.

Another embodiment provides a method of chelating and quantifying copper using compositions containing a compound of Formula I, II, III, IV, V, VI, or VII or an enantiomer, polymorph or salt thereof conjugated to a detectable probe.

Also provided is a method of reducing the amount of labile copper in a subject in need thereof by administering to the subject one or more of the disclosed compounds in an amount effective to bind the labile copper and reduce the amount of labile copper in the subject, wherein the bound compound-copper complex is excreted from the subject. The subject can have a disease characterized by increased copper levels. Diseases characterized by increased copper levels can be selected from the group comprising Wilson's Disease, diabetes, obesity, cancer, and neurological disorders. Neurological disorders can be selected from the group consisting of Alzheimer's Disease, Parkinson's Disease, and Huntington's Disease. The cancer can be selected from the group consisting of colorectal, hairy cell leukemia, melanoma, non-small cell lung-cancer (NSCLC), thyroid cancer, lymphoma, reticulum cell sarcoma, bronchogenic and laryngeal squamous cell carcinomas, cervical, breast, stomach, and lung cancers.

Another embodiment provides a method of delivering copper to a subject in need thereof, by administering to the subject one or more of the disclosed compounds in an amount effective to increase the levels of copper in the subject, wherein the compounds are pre-bound with copper before being administered to the subject. The subject in need thereof can have a disease characterized by low copper levels such as Menkes disease.

BRIEF DESCRIPTION OF THE DRAWINGS

FIG. 1A-1B represents the structures of first-generation ligands PSP-1 (FIG. 1A) and PSP-2 (FIG. 1). FIG. 1C represents the preorganization of the ligand conformation through a bridging unit. FIG. 1D-1E represents the structures of two prototypes, phenPS (FIG. 1D) and naphPS (FIG. 1E), realized and characterized in this disclosure.

FIGS. 2A-2D are representative ORTEP drawings and atomic numbering schemes for the crystal structures of (FIG. 1A) phenPS, (FIG. 1B) [Cu(I)phenPS]$BF_4$, (FIG. 1C) naphPS, and (FIG. 1D) [Cu(I)naphPS]$BF_4$. Ellipsoids shown represent 50% probability. Hydrogen atoms and counter ions have been omitted for clarity.

FIG. 3A shows representative $^1$H NMR (500 MHz) chemical shifts and coupling patterns for the dimethylphosphorothioylmethyl substituents of phenPS before the addition of 1 molar equivalent [$Cu(CH_3CN)_4$]$BF_4$ in DMSO-$d_6$. FIG. 3B represents $^1$H NMR (500 MHz) chemical shifts and coupling patterns for the dimethylphosphorothioylmethyl substituents of phenPS after the addition of 1 molar equivalent [$Cu(CH_3CN)_4$]$BF_4$ in DMSO-$d_6$. FIG. 3C shows representative $^1$H NMR (500 MHz) chemical shifts and coupling patterns for the dimethylphosphorothioylmethyl substituents of naphPS before the addition of 1 molar equivalent [$Cu(CH_3CN)_4$]$BF_4$ in DMSO-$d_6$. FIG. 3D shows $^1$H NMR (500 MHz) chemical shifts and coupling patterns for the dimethylphosphorothioylmethyl substituents of naphPS after the addition of 1 molar equivalent $[Cu(CH_3CN)_4]BF_4$ in DMSO-$d_6$. Due to line broadening, the spectra in the presence of Cu(I) were recorded at 80° C.

FIGS. 5A-5D, 5R, 5S, 5U, 5X, and 5AD represent various PSP-ligands with substituted carbocyclic derivatives. FIGS. 5E-5L, 5Q, 5V, 5W, 5Y, 5Z, 5AA, 5AB, 5AC, 5AE, 5AF, 5AH, and 5AI represent PSP-ligands with heterocycle-backbone derivatives. FIGS. 5M-5P, 5Q, and 5T represent PSP-ligands with multi-cyclic-backbone derivatives.

FIG. 13B is a fluorescence intensity image acquired with emission channels of 611-750 nm (BP2). FIG. 13C is the ratio image of BP2/BP1. FIG. 13D is the ratio image before addition of 10 μM CuGTSM. FIG. 13E is the after addition of 10 μM CuGTSM. FIG. 13F is the ratio image after addition of 50 μM PSP-2. FIG. 13G is the time course of the average ratio change for the region of interest indicated with a white circle in 13D. Asterisks indicate time points for the respective ratio images. FIG. 13H is the mean fluorescence ratio of the cytoplasmic region averaged over 20 cells (P values calculated for n=20 using a two-tailed test). FIG. 13I is the ratio image before addition of 1 mM DTDP. FIG. 13J is the ratio image a 5 minutes after addition of 1 mM DTDP. FIG. 13K is the ratio image 20 minutes after addition of 1 mM DTDP. FIG. 13L is the time course of the average ratio change for the region of interest indicated with a white circle in 13I. Asterisks indicate time points for the respective ratio images. FIG. 13M is the mean fluorescence ratio of the cytoplasmic region averaged over 20 cells (P values calculated for n=20 using a two-tailed test). FIG. 13N is the ratio image before addition of 1 mM DTDP in cells grown in medium supplemented with 50 μM $CuCl_2$. FIG. 13O is the ratio image 2 minutes after addition of 1 mM DTDP in cells grown in medium supplemented with 50 μM $CuCl_2$. FIG. 13P is the ratio image 37 minutes after addition of 1 mM DTDP in cells grown in medium supplemented with 50 μM $CuCl_2$. FIG. 13Q is the time course of the average ratio change for the region of interest indicated with a white circle in 13N. Asterisks indicate time points for the respective ratio images.

DETAILED DESCRIPTION OF THE INVENTION

I. Definitions

Figures 4A, 4B, 4C:
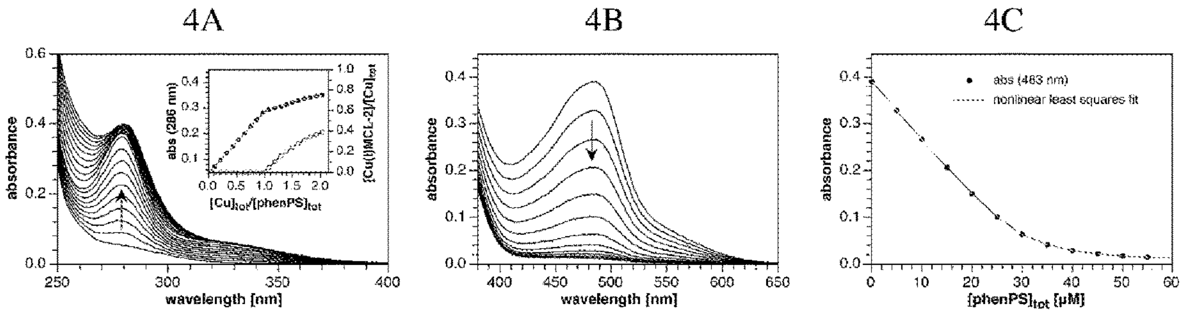
FIG. 4A shows the UV-vis traces for the molar ratio titration of phenPS with $[Cu(I)MCL\text{-}2]PF_6$.
FIG. 4B is the competition titration with phenPS with Cu(I) (30 μM, produced by in situ reduction with sodium ascorbate) in the presence of 1.5 mM BCS used for the determination of the Cu(I) binding affinities of phenPS in PIPES buffer (pH 7.0, 10 mM, 0.1 M KCl, 25° C.).
FIG. 4C represents the change of absorbance at 483 nm for the titration in plot 4B and non-linear least squares fit based on data from 400-650 nm.

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

Compounds discussed in the present invention can exist as stereoisomers when stereogenic centers are present.

To the extent that structures provided herein are compounds with tautomers by hydrogen migration, a skilled artisan would understand the formula to cover all tautomeric forms.

As used herein, "alkyl" refers to a noncyclic straight chain or branched, unsaturated or saturated hydrocarbon such as those containing from 1 to 10 carbon atoms, typically 1 to 30 otherwise designated $C_1$-$C_{30}$ alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, l-butynyl, 2-butynyl, 1-pentynyl, 2-pentynyl, 3-methyl-1-butynyl, and the like.

As used herein, "polycyclic" refers to any cyclic compound with more than one carbocycles and/or heterocycles either fused or bridged. Polycyclic groups can be optionally substituted. Polycyclic groups include, but are not limited to, 2,3,6,7-tetrahydro-1H,5H-pyrido[3,2,1-ij]thieno[2,3,f]quinoline, biphenyl, bithienyl, bipyridyl, naphthalene, 2,3,5,6,7,13-hexahydro-1H-indeno[2,1-j]pyrido[3,2,1-ij]quinoline, and 4,4-difluoro-4-bora-3a,4a-diaza-s-indacene.

As used herein, "carbocycle" refers to alkyl groups having a hydrocarbon ring, particularly to those having rings of 3 to 7 carbon atoms. Carbocycle groups include those with alkyl group substitution on the ring. Carbocycle groups can include straight-chain and branched-chain portions. Carbocycle groups can include aromatic carbocycles. Carbocycle groups include but are not limited to cyclopropyl, cyclobutyl, cyclopentyl, cyclohexyl, cycloheptyl, cyclooctyl, cyclononyl, and phenyl. Carbocycle groups can optionally be substituted. Carbocycle groups can be saturated or unsaturated.

As used herein, "heterocycle" refers to cyclic systems containing one to three heteroatoms in the ring, the remainder being carbon atoms. Suitable heteroatoms include, but are not limited to, oxygen, nitrogen, and sulfur. Heterocyclic groups include, but are not limited to, pyridine, morpholine, furan, thiophene, pyrrole, N-alkyl pyrrole, pyrrolidine, pyrimidine, pyrazine, imidazole, benzofuran, benzothiophene, quinoline, indole, azetidine, diazetidine, oxazole, piperidine, pyran, tetrahydrofuran, and dioxane. Heterocycle groups can be optionally substituted. Heterocycle groups can be saturated or unsaturated.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts or sodium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "carrier" refers to an organic or inorganic ingredient, natural or synthetic, with which the active ingredient is combined to facilitate the application.

The term "pharmaceutically acceptable" means a non-toxic material that does not interfere with the effectiveness of the biological activity of the active ingredients.

The term "pharmaceutically-acceptable carrier" means one or more compatible solid or liquid fillers, dilutants or encapsulating substances which are suitable for administration to a human or other vertebrate animal.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "subject," and "patient" are used interchangeably herein, and refer to a mammal, including, but not limited to, humans, rodents, such as mice and rats, and other laboratory animals.

II. Compositions for Chelating Copper(I)

Compounds that chelate copper(I) and methods of their use are provided. Exemplary compounds are described below. The compounds are useful for chelating copper(I), quantifying copper(I) in a sample, imaging copper(I) in cells or tissues, and treating copper(I)-related illnesses and conditions.

A. Copper-Chelating Compounds

One embodiment provides a copper chelating compound including but not limited to the following: FIG. 5A—ammonium 3,4-bis(bis((dimethylphosphorothioyl)methyl)phosphaneyl)benzenesulfonate; FIG. 5B—3,4-bis(bis((dimethylphosphorothioyl)methyl)phosphaneyl)benzoic acid; FIG. 5C—N-(2-aminoethyl)-3,4-bis(bis((dimethylphosphorothioyl)methyl)phosphaneyl)benzamide; FIG. 5D—N-(2-aminoethyl)-3,4-bis(bis((dimethylphosphorothioyl)methyl)phosphaneyl)benzamide tethered to a bioconjugate; FIG. 5E—((pyridine-3,4-diylbis(phosphanetriyl))tetrakis(methylene))tetrakis(dimethylphosphine sulfide); FIG. 5F—3-(3,4-bis(bis((dimethylphosphorothioyl)methyl)phosphaneyl)pyridin-1-ium-1-yl)propane-1-sulfonate; FIG. 5G—((pyridazine-4,5-diylbis(phosphanetriyl))tetrakis(methylene))tetrakis(dimethylphosphine sulfide); FIG. 5H—((pyrazine-2,3-diylbis(phosphanetriyl))tetrakis(methylene))tetrakis(dimethylphosphine sulfide); FIG. 5I—substituted ((thiophene-2,3-diylbis(phosphanetriyl))tetrakis(methylene))tetrakis(dimethylphosphine sulfide); FIG. 5J—substituted 4,5-bis(bis((dimethylphosphorothioyl)methyl)phosphaneyl)furan-2-carboxylic acid; FIG.

5K—substituted (((1-methyl-1H-imidazole-4,5-diyl)bis(phosphanetriyl))tetrakis(methylene))tetrakis(dimethylphosphine sulfide); FIG. 5L: substituted ((thiazole-4,5-diylbis(phosphanetriyl))tetrakis(methylene))tetrakis(dimethylphosphine sulfide); FIG. 5M—(((oxybis(2,1-phenylene))bis(phosphanetriyl))tetrakis(methylene))tetrakis(dimethylphosphine sulfide); FIG. 5N—(((thiobis(2,1-phenylene))bis(phosphanetriyl))tetrakis(methylene))tetrakis(dimethylphosphine sulfide); FIG. 5O—(((azanediylbis(2,1-phenylene))bis(phosphanetriyl))tetrakis(methylene))tetrakis(dimethylphosphine sulfide); FIG. 5P—(((9,9-dimethyl-9H-xanthene-4,5-diyl)bis(phosphanetriyl))tetrakis(methylene))tetrakis(dimethylphosphine sulfide); FIG. 5Q—substituted ((quinolin-8-ylphosphanediyl)bis(methylene))bis(dimethylphosphine sulfide); FIG. 5R—(((2-(dimethylphosphorothioyl)phenyl)phosphanediyl)bis(methylene))bis(dimethylphosphine sulfide); FIG. 5S: (((2-mercaptophenyl)phosphanediyl)bis(methylene))bis(dimethylphosphine sulfide); and FIG. 5T: (([1,1'-biphenyl]-2,2'-diylbis(phosphanetriyl))tetrakis(methylene))tetrakis(dimethylphosphine sulfide); FIG. 5S—(((2-mercaptophenyl)phosphanediyl)bis(methylene))bis(dimethylphosphine sulfide); FIG. 5T—(([1,1'-biphenyl]-2,2'-diylbis(phosphanetriyl))tetrakis(methylene))tetrakis(dimethylphosphine sulfide); FIG. 5U—((cyclopent-1-ene-1,2-diylbis(phosphanetriyl))tetrakis(methylene))tetrakis(dimethylphosphine sulfide); FIG. 5V—(((2,5-dihydro-1H-pyrrole-3,4-diyl)bis(phosphanetriyl))tetrakis(methylene))tetrakis(dimethylphosphine sulfide); FIG. 5W—(((2,5-dihydrofuran-3,4-diyl)bis(phosphanetriyl))tetrakis(methylene))tetrakis(dimethylphosphine sulfide); FIG. 5X—((cyclohex-1-ene-1,2-diylbis(phosphanetriyl))tetrakis(methylene))tetrakis(dimethylphosphine sulfide); FIG. 5Y—(((1,2,5,6-tetrahydropyridine-3,4-diyl)bis(phosphanetriyl))tetrakis(methylene))tetrakis(dimethylphosphine sulfide); FIG. 5Z—4,5-bis(bis((dimethylphosphorothioyl)methyl)phosphaneyl)-3,6-dihydro-2H-thiopyran 1,1-dioxide; FIG. 5AA—(((2-(dimethylphosphorothioyl)-5-(2,3,6,7-tetrahydro-1H,5H-pyrido[3,2,1-ij]thieno[2,3-f]quinolin-10-yl)thiophen-3-yl)phosphanediyl)bis(methylene))bis(dimethylphosphine sulfide); FIG. 5AB—(((5-(13,13-dimethyl-2,3,5,6,7,13-hexahydro-1H-indeno[2,1-f]pyrido[3,2,1-ij]quinolin-11-yl)thiophene-2,3-diyl)bis(phosphanetriyl))tetrakis(methylene))tetrakis(dimethylphosphine sulfide); FIG. 5AC—(((3-(bis((dimethylphosphorothioyl)methyl)phosphaneyl)-5-(5-(4-(dimethylamino)phenyl)thiazol-2-yl)thiophen-2-yl)phosphanediyl)bis(methylene))bis(dimethylphosphine sulfide); FIG. 5AD—(E)-2-(3-(bis((dimethylphosphorothioyl)methyl)phosphaneyl)-2-mercaptostyryl)-1,3,3-trimethyl-3H-indol-1-ium, FIG. 5AE—(((3-(1,3-dimethyl-2-sulfido-1,3,2-diazaphospholidin-2-yl)thiophen-2-yl)phosphanediyl)bis(methylene))bis(dimethylphosphine sulfide); FIG. 5AF—(E)-(((5-(4-(dimethylamino)styryl)-3-(dimethylphosphorothioyl)thiophen-2-yl)phosphanediyl)bis(methylene))bis(dimethylphosphine sulfide); FIG. 5AG—(E)-(((5-(4-(dimethylamino)styryl)-3-(dimethylphosphorothioyl)thiophen-2-yl)phosphanediyl)bis(methylene))bis(dimethylphosphine sulfide); FIG. 5AH—(((5'-(4-(dimethylamino)phenyl)-4-(dimethylphosphorothioyl)-[2,2'-bithiophen]-5-yl)phosphanediyl)bis(methylene))bis(dimethylphosphine sulfide); and FIG. 5AI—(((4-(6-(dimethylamino)benzo[b]thiophen-2-yl)-1,2-phenylene)bis(phosphanetriyl))tetrakis(methylene))tetrakis(dimethylphosphine sulfide).

In other embodiments the copper chelating compounds include but are not limited to the copper chelating compounds according to Formulas I, II, III, IV, V, VI and VII.

One embodiment provides a compound according to Figure I:

(Formula I)

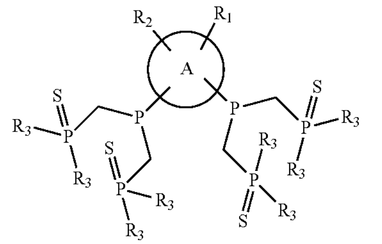

wherein:

A is any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, ferrocene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

$R_1$ and $R_2$ are independently selected from —H, -halogen, —$NH_2$, —$CONH_2$, —$NO_2$, —$CH_3$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —$C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$;

$R_3$ is selected from —$C_1$-$C_{30}$ alkyl, —NH($C_1$-$C_{30}$ alkyl), —N($C_1$-$C_{30}$ alkyl)$_2$, —O($C_1$-$C_{30}$ alkyl)OH, or —S($C_1$-$C_{30}$ alkyl)SH; and $R_4$ is selected from halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

Another embodiment provides a compound according to Formula II:

(Formula II)

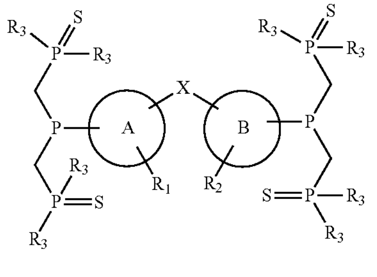

wherein:

A and B are independently any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, ferrocene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

X is selected from —O—, —S—, —N(H)—, —N(alkyl)-, —$C_1$-$C_{30}$ alkyl-, —$C_1$-$C_{30}$ alkyl-O—$C_1$-$C_{30}$ alkyl-, —$C_1$-$C_{30}$ alkyl-N—$C_1$-$C_{30}$ alkyl-, or —$C_1$-$C_{30}$ alkyl-S—$C_1$-$C_{30}$ alkyl-;

$R_1$ and $R_2$ are independently selected from —H, -halogen, —$NH_2$, —$CONH_2$, —$NO_2$, —$CH_3$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —$C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$; and $R_3$ is selected from —$C_1$-$C_{30}$ alkyl, —NH($C_1$-$C_{30}$ alkyl), —N($C_1$-$C_{30}$ alkyl)$_2$, —O($C_1$-$C_{30}$ alkyl)OH, or —S($C_1$-$C_{30}$ alkyl)SH; and $R_4$ is selected from -halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

Another embodiment provides a compound according to Formula III:

(Formula III)

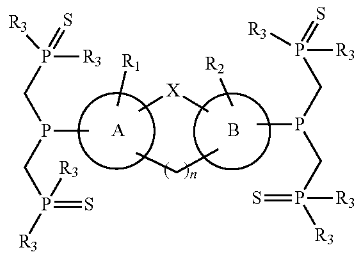

wherein:

A and B are independently any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

X is selected from —O—, —S—, —N(H)—, —N(alkyl)-, —$C_1$-$C_{30}$ alkyl-, —$C_1$-$C_{30}$ alkyl-O—$C_1$-$C_{30}$ alkyl-, —$C_1$-$C_{30}$ alkyl-N—$C_1$-$C_{30}$ alkyl-, or —$C_1$-$C_{30}$ alkyl-S—$C_1$-$C_{30}$ alkyl-;

$R_1$ and $R_2$ are independently selected from —H, -halogen, —$NH_2$, —$CONH_2$, —$NO_2$, —$CH_3$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), $C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$; and $R_3$ is selected from —$C_1$-$C_{30}$ alkyl, —NH($C_1$-$C_{30}$ alkyl), —N($C_1$-$C_{30}$ alkyl)$_2$, —O($C_1$-$C_{30}$ alkyl)OH, or —S($C_1$-$C_{30}$ alkyl)SH; and $R_4$ is selected from -halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

n is selected from zero to five;

Another embodiment provides a compound according to Formula IV:

(Formula IV)

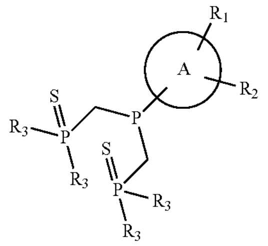

wherein:

A is any aromatic system including but not limited to anthracene, azepine, benzene, benzimidazole, benzofuran, benzothiophene, bifuran, biphenyl, bipyridyl, bithiophene, chrysene, cinnoline, cyclopentadienyl, 9,9-dimethyl-xanthene, ferrocene, furan, imidazole, indazole, indole, indoxazine, isoquinoline, isothiazole, isoxazole, methylimidazole, methylindole, naphthalene, oxadiazole, oxazole, phenanthrene, phenanthroline, phthalazine, pteridine, pyrazole, pyrazine, pyrene, pyridine, pyrilium, pyrimidine, pyrrole, quinoline, quinolone, quinoxaline, quinazoline, thiadiazole, thiazole, thiophene, triazole, or xanthene;

$R_1$ is independently selected from —H, -halogen, —$NH_2$, —$CONH_2$, —$NO_2$, —$CH_3$, —$SO_3H$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, $C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$;

$R_2$ is independently selected from —H, -halogen, —$NH_2$, —O—($C_1$-$C_{30}$ alkyl), —NH—($C_1$-$C_{30}$ alkyl), —S—($C_1$-$C_{30}$ alkyl), —N($C_1$-$C_{30}$ alkyl)($C_1$-$C_{30}$ alkyl), —OH, —SH, —C(S)SH, —C(O)SH, —COO($C_1$-$C_{30}$ alkyl), any aromatic system including but not limited to triazole, tetrazole, imidazole, pyrazole, pyridine, pyrimidine optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$, -(phosphanediylbis(methylene))bis(dimethylphosphine sulfide), -dimethylphosphine sulfide, —$P(R_5)_2$, —$P(S)(R_5)_2$, or —$P(O)(R_5)_2$;

$R_3$ is selected from —$C_1$-$C_{30}$ alkyl, —NH($C_1$-$C_{30}$ alkyl), —N($C_1$-$C_{30}$ alkyl$)_2$, —O($C_1$-$C_{30}$ alkyl)OH, or —S($C_1$-$C_{30}$ alkyl)SH; and $R_4$ is selected from -halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, or —$C_1$-$C_{30}$ alkyl; and $R_5$ is selected from —OH, —SH, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), $C_1$-$C_{30}$ alkyl which can be optionally substituted with $R_4$, any aromatic system optionally substituted with $R_4$, a carbocycle or heterocycle optionally substituted with $R_4$, or a polycyclic carbocycle or heterocycle optionally substituted with $R_4$;

or an enantiomer, polymorph or salt thereof.

Another embodiment provides a compound according to Formula V:

(Formula V)

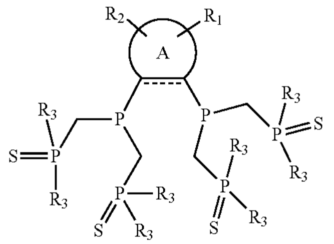

wherein:

A is any monocyclic or polycyclic saturated or unsaturated aliphatic or heteroaliphatic system including but not limited to azetidine, aziridine, cyclobutane, cyclobutene, cyclohexane, cyclohexene, cyclopropane, cylopropene, cyclopentene, cyclopentane, oxetane, norbornane, norbornene, piperidine, pyrrolidine, pyrimidine, tetrahydrofuran, thietane, thiolane, thiolane, thiolane-1-oxide, thiolane-1,1-dioxide; and $R_1$ and $R_2$ are independently selected from —H, —O—($C_1$-$C_{30}$ alkyl), —NH—($C_1$-$C_{30}$ alkyl), —$SO_3$H, —COOH, —S—($C_1$-$C_{30}$ alkyl), —N($C_1$-$C_{30}$ alkyl)($C_1$-$C_{30}$ alkyl), —OH, —SH, —COO($C_1$-$C_{30}$ alkyl), —CON—($C_1$-$C_{30}$ alkyl)-N—($C_1$-$C_{30}$ alkyl)-OH, —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —$C_1$-$C_{30}$ alkyl which can be optionally substituted with $R_4$, an aromatic system optionally substituted with $R_4$, a polycyclic aromatic system optionally substituted with $R_4$, a carbocycle or heterocycle optionally substituted with $R_4$, a polycyclic carbocycle or heterocycle optionally substituted with $R_4$, —($C_1$-$C_{30}$ alkyl)-carbocycle or heterocycle optionally substituted by $R_4$, —($C_1$-$C_{30}$ alkyl)-polycyclic carbocycle or heterocycle optionally substituted by $R_4$, -1,3-dimethyl-1,3,2-diazaphospholidine 2-sulfide, (phosphanediylbis(methylene))bis(dimethylphosphine sulfide), or -dimethylphosphine sulfide;

$R_3$ is selected from —$C_1$-$C_{30}$ alkyl, —NH($C_1$-$C_{30}$ alkyl), —N($C_1$-$C_{30}$ alkyl$)_2$, —O($C_1$-$C_{30}$ alkyl)OH, or —S($C_1$-$C_{30}$ alkyl)SH;

$R_4$ is selected from -halogen, —$NO_2$, —$NH_2$, —O—($C_1$-$C_{30}$ alkyl), —NH—($C_1$-$C_{30}$ alkyl), —S—($C_1$-$C_{30}$ alkyl), N($C_1$-$C_{30}$ alkyl)($C_1$-$C_{30}$ alkyl), —$CONH_2$, —CON($C_1$-$C_{30}$ alkyl)($C_1$-$C_{30}$ alkyl), —$SO_2$($C_1$-$C_{30}$ alkyl), —$SO_2$N($C_1$-$C_{30}$ alkyl)($C_1$-$C_{30}$ alkyl), —OH, —SH, —COO($C_1$-$C_{30}$ alkyl), —COOH, —$C_1$-$C_{30}$ alkyl;

or an enantiomer, polymorph or salt thereof.

Another embodiment provides a compound according to Formula VI:

(Formula VI)

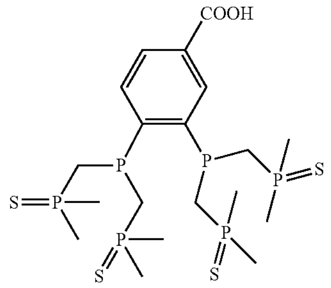

or an enantiomer, polymorph or salt thereof.

Still another embodiment provides for the compound according to Formula VII:

(Formula VII)

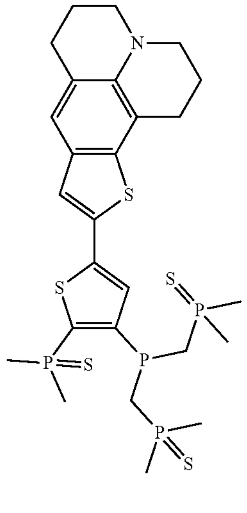

or an enantiomer, polymorph or salt thereof.

1. Conjugates

Some embodiments provide conjugates of the disclosed copper(I) chelator compounds wherein the copper(I) chelator compound is conjugated to a second compound including but not limited to targeting moieties, proteins, peptides, antibodies, probes, markers, or labels. The moieties can be conjugated to the compounds to serve as detection agents, to deliver the compounds to specific cells or tissues, to deliver the compounds to specific subcellular locations, or a combination thereof.

In one embodiment, the disclosed compounds are conjugated with a moiety that delivers the compounds to specific cells or tissues, or to specific subcellular locations. In such an embodiment, the compound is conjugated with a moiety that targets a protein or receptor that is present on the desired tissue, cell type, or subcellular location. In one embodiment, the moiety is an antibody that binds to a receptor on the target cell. In another embodiment, the moiety is a small molecule that binds to a receptor on the target cell. In yet another embodiment, the moiety is a sugar molecule, a glycolytic enzyme, or folate. In some embodiments the compounds of Formula I-VII are conjugated to glucuronic acid or a bile acid such as cholic, ursodeoxycholic, or cholylglycine to target the liver in vivo.

In one embodiment, the disclosed copper(I) chelator compounds are conjugated to a biomolecule. In certain embodiments, the biomolecule includes but is not limited to a protein, antibody, small biomolecule, biotin, or biological ligands. The term "biological ligands" refers to protein receptors, lipid receptors, polysaccharide receptors, lipopolysaccharide receptors, glycolipids, and their biological ligands. The protein receptor can be intracellular or express on the cell surface. For example, the asialoglycoprotein receptor (ASGP-R) is uniquely expressed at the plasma membrane of hepatocytes and can be specifically targeted by conjugating the chelator compound to galactose or N-acetylgalactosamine (GalNAc) (Ashwell, G.; Harford, J., *Ann. Rev. Biochem.* 1982, 51, 531-54).

In another embodiment, the disclosed compounds are conjugated to one or more detection agents. Exemplary detection agents include but are not limited to fluorophores, isotope markers, colorimetric labels, biotin/avidin, fluorogens, or mass tags.

In one embodiment, detection labels or proteins can be conjugated to the compounds using a self-labeling protein tag including, but not limited to SNAP, CLIP, or a Halo tag. SNAP-tag is a self-labeling protein tag which includes 182 residue polypeptide (19.4 kDa) that can be fused to any protein of interest and further specifically and covalently tagged with a suitable ligand, such as a fluorescent dye. CLIP-tag is an orthogonal tag further engineered from SNAP-tag to accept 2-benzylcytosine derivatives as substrates, instead of 6-benzylguanine. The HaloTag is a modified bacterial enzyme designed to covalently bind to a synthetic ligand of choice and fuse to a protein of interest. The HaloTag includes two covalently bound segments including a haloalkane dehalogenase and a synthetic ligand which can be chosen to suit the experiment. As such, the probe can include linking moieties, such as amide linker, through which additional compounds can be linked, for example an active ester for conjugation to amines, maleimide for thiol-selective conjugation, or an azide or alkyne for Cu-catalyzed alkyne-azide 1,3-dipolar cycloaddition (click chemistry). In another embodiment, the compound is conjugated to an aptamer.

In some embodiments, the compound is conjugated via a cleavable linker or group. Cleavable groups include Groups that are cleavable via enzymatic cleavage or cleavage by external stimuli such as pH or light. Groups that are cleaved via enzymatic cleavage include, but are not limited to, peptide linkers (Phe-Lys, Val-Ala, Val-Cit, Glu-Val-Cit), thioethers, β-glucuronide, β-galactoside, pyrophosphate, esters, and arylsulfates. Groups that are cleaved via light include, but are not limited to, substituted nitrobenzyl groups, substituted phenacyl groups, and substituted benzyl groups. Other cleavable groups include hydrazones, and disulfides.

B. Formulations

Another embodiment provides pharmaceutical formulations containing one or more of compounds according to Formula I, II, III, IV, V, VI, or VII or an enantiomer, polymorph, or pharmaceutically acceptable salt thereof or a conjugate thereof.

1. Delivery Vehicles

Compounds of Formula I, II, III, IV, V, VI, or VII can be administered to a subject, preferably a human subject, where it is taken up into the cells of a subject with or without the aid of a delivery vehicle. Appropriate delivery vehicles for the disclosed active agents are known in the art and can be selected to suit the particular active agent. For example, in some embodiments, the compound is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

In some embodiments, compounds according to Formula I, II, III, IV, V, VI, VII or an enantiomer, polymorph, or pharmaceutically acceptable salt thereof and a second therapeutic agent are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

The compounds according to Formula I, II, III, IV, V, VI, VII or an enantiomer, polymorph, or pharmaceutically acceptable salt thereof can be incorporated into a delivery vehicle prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. The release point and/or period of release can be varied as discussed above.

2. Pharmaceutical Compositions

One embodiment provides pharmaceutical compositions containing one more of the disclosed copper(I) chelator compounds formulated for administration by parenteral (intramuscular, intraperitoneal, intravenous (IV) or subcutaneous injection), or enteral, routes of administration or using bioerodible inserts and can be formulated in dosage forms appropriate for each route of administration.

In certain embodiments, the compositions are administered locally, for example by injection directly into a site to be treated (e.g., into a tumor). In some embodiments, the compositions are injected or otherwise administered directly into the vasculature onto vascular tissue at or adjacent to the intended site of treatment (e.g., adjacent to a tumor). Typically, local administration causes an increased localized concentration of the composition which is greater than that which can be achieved by systemic administration.

a. Formulations for Parenteral Administration

Compounds according to Formula I, II, III, IV, V, VI, VII or an enantiomer, polymorph, or pharmaceutically acceptable salt thereof and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Formulations for Enteral Formulations

Compounds according to Formula I, II, III, IV, V, VI, VII or an enantiomer, polymorph, or pharmaceutically acceptable salt thereof can be formulated for enteral administration. Suitable oral dosage forms of compounds of Formula I, Formula II, Formula III, Formula IV, Formula V, Formula VI, Formula VII, or an enantiomer, polymorph, or pharmaceutically acceptable salt thereof include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation into the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropylcellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain embodiments, the acrylic polymer is comprised of one or more ammonium methacrylate copolymers. Ammonium methacrylate copolymers are well known in the art and are described as fully polymerized copolymers of acrylic and methacrylic acid esters with a low content of quaternary ammonium groups.

In one embodiment, the acrylic polymer is an acrylic resin lacquer such as that which is commercially available from Rohm Pharma under the trade name Eudragit®. In further preferred embodiments, the acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules, etc.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a “coated core” dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional “enteric” polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., dimethicone), may also be added to the coating composition.

III. Methods of Use

The disclosed compounds are useful for chelating copper in industrial samples, environmental samples, biological samples or within living biological systems. In other embodiments, the compounds can be used to chelate copper in industrial applications. In addition, the compounds can be used to detect and remove copper from biological samples or living systems. In biological systems, the intra-cellular and extra-cellular metabolism of copper is under tight control, in order to maintain free copper concentrations at very low levels. Copper is a critical element for proper functioning of many biological systems, and both the accumulation of copper and copper deficiency are associated with various diseases and disorders. As such, the disclosed copper chelators can be used to treat or reduce the symptoms of diseases that are characterized by dysregulated copper levels or dysregulated copper trafficking by reducing plasma or tissue levels of labile copper through the excretion of the chelating compound-copper complex.

In another embodiment, the disclosed compounds can be pre-loaded with copper and administered to a subject in need of copper. In such an embodiment, the copper is coordinated to the compound in such a manner that the copper dissociates from the compound once it has reached a target tissue, organ, or cell. In some embodiments, the release could be triggered through competitive chelation by endogenous ligands of higher affinity, by a lower pH within a cellular compartment, or by a change in redox potential that would invoke oxidation of the phosphine moiety. In some embodiments, the disclosed compounds are conjugated to a probe via a cleavable group, when the group is cleaved copper is released. Cleavable groups include groups that are cleavable via enzymatic cleavage or cleavage by external stimuli such as pH or light. Groups that are cleaved via enzymatic cleavage include, but are not limited to, peptide linkers (Phe-Lys, Val-Ala, Val-Cit, Glu-Val-Cit), thioethers, β-glucuronide, β-galactoside, pyrophosphate, esters, and arylsulfates. Groups that are cleaved via light include, but are not limited to, substituted nitrobenzyl groups, substituted phenacyl groups, and substituted benzyl groups. Other cleavable groups include hydrazones, and disulfides.

A. Methods of Separating and Quantifying Copper(I)

The disclosed compositions for chelating copper(I) can be used as probes for separating and/or quantifying copper(I) in complex mixtures. The complex mixtures can be biological samples, such as blood, plasma, urine, tissue, tumor tissue, feces, cerebrospinal fluid, cell lysate or any other biological sample in which copper levels are required to be determined.

In some embodiments, the compounds according to Formula I, II, III, IV, V, VI, VII or an enantiomer, polymorph, or salt thereof are used in a variety of metal detecting methods, including, but not limited to UV-vis absorption spectroscopy, steady-state fluorescence spectroscopy, time-resolved fluorescence spectroscopy, time-resolved fluorescence imaging, single-photon fluorescence microscopy, confocal laser scanning microscopy, multi-photon excitation microscopy, nuclear magnetic resonance spectroscopy, nuclear magnetic resonance imaging, photoacoustic spectroscopy, or photoacoustic tomography.

In one embodiment, the copper chelating compounds are contacted with the sample directly either in biological samples or industrial samples. In such an embodiment, the compounds are added directly into the sample, i.e. a liquid sample, and incubated for a period of time. The incubation period can be minutes or hours. In one embodiment the incubation period can be 1 minute, 2 minutes, 3 minutes, 4 minutes, 5 minutes, 6 minutes, 7 minutes, 8 minutes, 9 minutes, 10 minutes, 15 minutes, 30 minutes, 1 hour, 2 hours, 3 hours, 4 hours, 5 hours, 6 hours, 12 hours, 24 hours, or 1-24 hours. After an incubation period, the compound-sample mixture is subjected to a detection method. In one embodiment, the chelating compound has a detection agent conjugated to it and the amount of the detection agent is comparable to the amount of copper present. In another embodiment, the chelating compound is conjugated with magnetic beads and the compound-copper complex is removed from the sample using a magnetic column. In such an embodiment, the copper can then be measured after the magnetic separation.

In another embodiment the source of the copper to be chelated is from copper(II). For example, copper(II) can be reduced in a sample by adding a reducing agent. Exemplary reducing agents include but are not limited to sodium ascorbate, glutathione, dihydrolipoic acid, hydroxylamine, dithiothreitol (DTT), triphenyl phosphine, mercaptoethanol, tris(2-carboxyethyl)phosphine (TCEP), 2,3-dimercaptopropanesulfonate (DMPS), 2-mercaptoethanesulfonate (MESNA), (2S)-2-amino-1,4-dimercaptobutane (DTBA), sodium ascorbate, and hydroxylamine. The copper chelating compounds can then chelate the copper(I) produced from the reduction of copper(II) in the sample. The sample can be a biological sample or an industrial sample. The copper chelating compounds can then chelate the copper(I) produced from the reduction of copper(II) in the sample. The sample can be a biological sample or an industrial sample.

Exemplary methods for quantifying copper in biological samples (or other samples, such as environmental or industrial samples) include but are not limited to the following:

1) Analysis of total copper content by spectroscopic methods (UV-vis spectroscopy, fluorescence spectroscopy):

A known quantity of the biological sample is digested with a strong mineral acid such as concentrated nitric acid (analytical grade). An aliquot of the digested solution is transferred to a buffer (pH 7, 0.1 M KCl, including sodium ascorbate (150 μM) as reducing agent) containing a precise concentration of the chelating ligand that exhibits a different absorption spectrum or fluorescence excitation or emission spectrum of the free compared to the Cu(I)-bound form. Using spectra of the free and Cu(I) saturated chelating ligand as reference (determined in a separate experiment), the fractional saturation of the chelating ligand can be determined (as there is a linear relationship between spectral change and total copper bound to the ligand). Based on the fractional saturation, the total concentration of copper in the sample can be calculated.

2) Analysis of the Cu(I) activity (buffered concentration) in a biological sample (e.g. within the cytosol of a cell):

For this application, a fluorescent chelator that responds with a shift of excitation or emission spectrum is employed. Based on the ratio of intensity at two distinct wavelengths, the fractional saturation of the chelator can be determined using ratiometric analysis as described in the original report by Tsien and coworkers (Grynkiewicz, G.; Poenie, M.; Tsien, R. Y., *J. Biol. Chem.* 1985, 260 (6), 3440-3450). For a ratiometric fluorescent chelator probe P with 1:1 Cu(I)-probe binding stoichiometry, the ratio R of the fluorescence intensities at two distinct wavelengths is related to the activity [Cu(I)](free buffered concentration) according to equation 1, $$[\mathrm{Cu(I)}] = K_d\left(\frac{R - R_{min}}{R_{max} - R}\right)\left(\frac{S_f}{S_b}\right) \tag{1}$$

where $K_d$ is the dissociation constant of the Cu(I)-probe complex (Cu(I)P), $R_{min}$ and $R_{max}$ are the fluorescence intensity ratios for the free and Cu(I)-saturated probe, respectively, and $S_f$ and $S_b$ are instrument-dependent calibration factors for the free ($S_f$) and metal-bound ($S_b$) probe. The concentration of each species is related to the overall fluorescence intensity F at wavelength λ according to equation 2

$$F(\lambda)=S_f(\lambda)[P]+S_b(\lambda)[Cu(I)P] \tag{2}$$

If λ is selected where the emission spectra of the free (P) and Cu(I)-saturated probe (Cu(I)P) cross each other, $S_f$ and $S_b$ are identical and thus the instrument-dependent correction term $S_f/S_b$ assumes unity. Hence, under these conditions the intensity ratio R can be related to the activity of Cu(I) according to equation (3)

$$[\mathrm{Cu(I)}] = K_d\left(\frac{R - R_{min}}{R_{max} - R}\right) \tag{3}$$

Furthermore, the fractional saturation of the probe, defined as the ratio of complex concentration [Cu(I)

P] and total chelator concentration $[P]_{total}$, can be calculated from the observed intensity ratio R using equation (4)

$$f = \frac{[Cu(I)P]}{[P]_{total}} = \frac{R - R_{min}}{R_{max} - R_{min}} \quad (4)$$

To determine the intracellular activity of Cu(I), cells are grown on glass bottom culture dishes (MatTek) to 70% confluency in DMEM supplemented with 10% FBS and Penicillin/Streptomycin. Before imaging, the media is replaced with pre-warmed DMEM supplemented with 10% FBS, penicillin/streptomycin, and 100 mM sodium pyruvate containing 1 μM of the fluorescent ratiometric chelator and incubated at 37° C. in 5% $CO_2$ for 20 minutes. For live cell studies, cells are imaged at 37° C. under a humidified 5% $CO_2$ atmosphere using a fluorescence microscope (such as a laser confocal fluorescence microscope or a two-photon excitation microscope equipped with a femtosecond pulsed Ti:sapphire laser). Fluorescence micrographs are acquired at a suitable excitation wavelength and emission is simultaneously collected over two channels with non-overlapping bandpass ranges BP1 and BP2 (for example 480-540 and 610-750 nm). Intensity ratio images are generated with a suitable software such as ImageJ by deriving the intensity ratio BP2/BP1 for each pixel.

In another embodiment, the disclosed compounds according to Formula I, II, III, IV, V, VI, VII, or an enantiomer, polymorph, or salt thereof are coated or immobilized on a support, either directly or indirectly bound via another substance. Supports include but are not limited to agarose, silica, alumina, glass plates, beads, organic polymers, inorganic compounds, or biopolymers. The sample to be quantified is contacted with the immobilized chelating compound for an amount of time. The sample can be incubated for seconds, minutes or hours. In one embodiment the incubation period can be 1 minute, 2 minutes, 3 minutes, 4 minutes, 5 minutes, 6 minutes, 7 minutes, 8 minutes, 9 minutes, 10 minutes, 15 minutes, 30 minutes, 1 hour, 2 hours, 3 hours, 4 hours, 5 hours, 6 hours, 12 hours, or 24 hours. In another embodiment, the chelator is incubated with the sample for 1-24 hours. After such a time has elapsed, the remaining sample is removed from the support using an appropriate buffer. The copper bound to the support is quantified either by detecting the copper directly on the support, or by separating the chelating compound and copper complex from the support by breaking the bond between the support and the binding substrate. In one embodiment, the disclosed compounds are conjugated with a fluorescent agent that is quenched when it is bound by copper. In such an embodiment, the level of fluorescence is inverse to the amount of copper present in the sample. The amount of the chelating compound placed into the sample should be recorded for calculating bound copper. In another embodiment, the disclosed compounds are conjugated with a fluorescent agent that is quenched when it is not bound by copper. In such an embodiment, the level of fluorescence is proportional to the amount of copper present in the sample. The amount of the chelating compound placed into the sample should be recorded for calculating bound copper. In another embodiment, the disclosed compounds are conjugated with a fluorescent probe that changes color upon copper binding. In such an embodiment, after the sample and the disclosed compounds have been incubated, the fluorescence intensity ratio at two different wavelengths is measured. This ratio is independent of the probe concentration in the sample if the probe binds Cu(I) with a 1:1 complex stoichiometry. Based on the fluorescence intensity ratio, the fractional saturation, which corresponds to the amount of copper bound to the chelator, can be calculated.

In one embodiment, the disclosed compounds can be used in a method to detect copper in a sample by performing the steps of (1) contacting the sample with one or more compounds according to Formula I, II, III, IV, V, VI, VII or an enantiomer, polymorph, or salt thereof conjugated with a fluorescent probe; (2) detecting a light emission of a first wavelength emission and a second wavelength emission, wherein the first wavelength emission intensity is associated with the unbound ligand, and the second wavelength emission intensity is associated with the copper (I)-bound ligand; and (3) comparing the first wavelength emission intensity to the second wavelength emission intensity to determine the amount of copper(I) in the system. In some embodiments, the method can further include excitation at a wavelength associated with the absorption of the compound according to Formula I, II, III, IV, V, VI, VII or an enantiomer, polymorph, or salt thereof.

A ratiometric probe such as, but not limited to, a compound composed of a conjugated π-system substituted with an electron-rich donor moiety according to Formula VII can also be employed to assess the size of the labile Cu(I)-pool (buffer depth) associated with biological thiols using a thiol-selective oxidant such as 2,2'-dithiodipyridine (DTDP). For example, when cells were grown with medium supplemented with 50 μM $CuCl_2$ for one week, only a small and statistically insignificant intensity ratio increase was observed (FIG. 13I-13M), despite the fact that the average total cellular copper levels increased by more than 2-fold as indicated by TXRF elemental analysis. However, when cells grown in copper-supplemented medium were treated with the thiol-selective oxidant 2,2'-dithiodipyridine (DTDP), a dramatic increase in fluorescence ratio up to 1.9 was observed (FIG. 13N-R), consistent with dissociation of a sizable pool of Cu(I) from sulfhydryl coordination sites. These data demonstrate that a ratiometric probe such as, but not limited, to a compound according to Formula VII in conjunction with DTDP can be used to assay the thiol-bound pool of cellular Cu(I) based on ratiometric imaging microscopy. In one embodiment, the ratiometric copper(I) chelator is -(((5-(13,13-dimethyl-2,3,5,6,7,13-hexahydro-1H-indeno[2,1-f]pyrido[3,2,1-ij]quinolin-11-yl)thiophene-2,3-diyl)bis(phosphanetriyl))tetrakis(methylene))tetrakis(dimethylphosphine sulfide)(FIG. 5AB).

B. Methods of Measuring Copper (I) Binding Affinities

In one embodiment, the disclosed compounds can be used for the measurement of reliable copper(I) protein binding affinities. In some embodiments, the disclosed compounds are employed in a competition titration with a reference chelator to measure copper(I) binding affinities. In some embodiments, the disclosed compounds are employed in a competition titration of the reference chelator copper(I)-complex with apo-protein (or free ligand).

C. Methods of Identifying Copper(I)-Binding Proteins

In one embodiment, the disclosed compounds can be employed to identify Cu(I)-binding proteins and other ligands in complex biological mixtures based on mass spectrometry proteomics analysis. In some embodiments, the complex mixtures are biological samples, such as blood, plasma, urine, tissue, tumor tissue, feces, cerebrospinal fluid, cell lysate or any other biological sample in which copper is bound to sulfhydryl (—SH)-ligands. In some embodiments, the biological mixture is incubated with the copper(I) chelating compound and a mass spectrometry isotope label or an isobaric labeling reagent such as iodoTMTsixplex (iodoTMT™ ThermoFisher Scientific).

D. Methods of Treating Copper(I)-Related Illnesses or Conditions

The disclosed compositions for selectively chelating copper(I) can be used to treat diseases in which copper(I) is incorrectly trafficked. Copper mistrafficking can lead to an increase in copper levels or a decrease in copper levels. In other embodiments, it can lead to a tissue or organ specific increase or decrease in copper concentration such that the systemic concentration is not dysregulated, just the concentration within the specific tissue or organ.

In some embodiments the copper(I) chelating compounds are used to therapeutically deliver copper to a subject with low copper levels, either systemically or organ/tissue specifically. In such an embodiment, the disclosed compound is loaded with copper before it is administered to the subject. The copper can be coordinated to the compound in such a manner that the copper either dissociates from the compound or is chelated by bioligands once it has reached a target tissue, organ, or cell. In such an embodiment, the copper is coordinated to the compound in such a manner that the copper dissociates from the compound once it has reached a target tissue, organ, or cell. In some embodiments, the release could be triggered through competitive chelation by endogenous ligands of higher affinity, by a lower pH within a cellular compartment, by a change in redox potential that would invoke oxidation of the phosphine moiety, enzymatic cleavage or reduction, or external stimuli.

In some embodiments, the disclosed compounds are conjugated to a probe via a cleavable group, when the group is cleaved copper is released. Cleavable groups include Groups that are cleavable via enzymatic cleavage or cleavage by external stimuli such as pH or light. Groups that are cleaved via enzymatic cleavage include, but are not limited to, peptide linkers (Phe-Lys, Val-Ala, Val-Cit, Glu-Val-Cit), thioethers, β-glucuronide, β-galactoside, pyrophosphate, esters, and arylsulfates. Groups that are cleaved via light include, but are not limited to, substituted nitrobenzyl groups, substituted phenacyl groups, and substituted benzyl groups. Other cleavable groups include hydrazones, and disulfides.

In another embodiment the copper(I) chelating compounds are used to therapeutically remove copper from a subject with high copper concentrations, either systemically or organ/tissue specific. In such an embodiment, after being administered to the subject, the disclosed compounds bind with labile copper, creating a compound-copper complex. The complex is removed from the body through excretion. The excretion can be salivary, urinary, or biliary. In some embodiments, the chelating compounds target a specific cell, tissue, or organ. In another embodiment, the chelating compounds enter into circulation and remove labile copper from the systemic circulation.

In some embodiments, the disclosed compounds or pharmaceutical composition including the compounds, are administered locally or regionally. For example, in some embodiments, compositions containing the disclosed compounds are delivered to or specifically target the tissue or organs in need of modulation.

In some in vivo approaches, the compositions disclosed herein are administered to a subject in a therapeutically effective amount. As used herein the term “effective amount” or “therapeutically effective amount” means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Exemplary symptoms, pharmacologic, and physiologic effects are discussed in more detail below.

In some embodiments, the effect of the composition on a subject is compared to a control. For example, the effect of the composition on a particular symptom, pharmacologic, or physiologic indicator can be compared to an untreated subject or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based measuring the symptom, pharmacologic, or physiologic indicator in one or more subjects that do not have the disease or condition to be treated (e.g., healthy subjects). In some embodiments, the effect of the treatment is compared to a conventional treatment that is known the art. For example, if the disease to be treated is cancer, a conventional treatment could a chemotherapeutic agent.

In some embodiments, the copper(I) chelating compositions disclosed herein are administered in combination with one or more additional active agents. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such formulations typically include an effective amount of one or more of the disclosed copper(I) chelating compounds. The different active agents can have the same, or different mechanisms of action. In some embodiments, the combination results in an additive effect on the treatment of the disease or disorder. In some embodiments, the combinations result in a more than additive effect on the treatment of the disease or disorder.

Compositions containing the disclosed compounds or an enantiomer, polymorph, or pharmaceutically acceptable salt thereof that chelate copper(I) can be used as a therapeutic agent in any disease state related to copper mistrafficking. Representative disease and disorders that may be treated using the disclosed compounds or an enantiomer, polymorph, or pharmaceutically acceptable salt thereof or compositions containing the disclosed compounds or an enantiomer, polymorph, or pharmaceutically acceptable salt thereof include, but are not limited to, Menkes disease, Wilson's disease, neurological disorders, obesity, diabetes, and cancer.

1. Menkes Disease

Menkes disease is a genetic disease caused by a genetic mutation in the ATP7A gene, which encodes a copper-transporting P-type ATPase that localizes to the trans-Golgi network and delivers copper to cuproenzymes within the secretory pathway. Copper is a necessary mineral for normal cellular function; however, it is toxic in high concentrations. In patients with Menkes disease, copper dysregulation leads to systemic copper deficiency due to impaired copper transport across enterocytes into the bloodstream.

One embodiment of the present invention provides a method for the treatment of Menkes disease by administering to a subject an effective amount of the disclosed compounds according to Formula I, II, III, IV, V, VI, or VII pre-bound with copper in an amount effective to deliver copper to the subject and maintain a healthy systemic copper concentration. In some embodiments, the compound used to deliver copper to the subject is designed such that it can act as a mild ionophore to redistribute mistrafficked copper, for example from enterocytes which are the location of the increased concentration of copper in subjects with Menkes disease, to the blood.

2. Wilson's Disease

Wilson's disease is a rare genetic disorder caused by a mutation in the ATP7B gene. ATP7B encodes for a copper-transporting P-type ATPase which plays a role in the transport of copper from the liver to other parts of the body, in particular the elimination of excess copper from the body. Wilson ATPase malfunction leads to excess copper build-up in the body, typically in the brain, eyes, and liver. If left untreated, Wilson's disease can lead to hepatic disease, central nervous system dysfunction, and death. In one embodiment, the disclosed compounds are useful for the treatment of Wilson's disease.

One embodiment of the present invention provides a method for the treatment of Wilson's disease by administering to a subject one or more of the disclosed compounds according to Formula I, II, III, IV, V, VI, VII or an enantiomer, polymorph, or pharmaceutically acceptable salt thereof, in an amount effective to reduce excess copper build up in the body. In such an embodiment, the copper chelating compound forms a complex with labile copper, and the complex is eliminated from the body through excretion. By reducing excess copper from the body, the symptoms of Wilson's disease can be eliminated or alleviated.

3. Neurological Disorders

Copper plays an important role in neurological function by participating in antioxidant defense and neurotransmitter synthesis. Copper deficiency or overload will ultimately result in neurological symptoms. Copper is one of the major transition elements in amyloid-beta plaque formation, a hallmark indicator of Alzheimer's disease. Mistrafficked copper is related to oxidative stress, alpha-synuclein oligomerization, and Lewy body formation; all of which are hallmark indications of Parkinson's disease. Copper also plays a role in Huntington's disease, and copper reduction has been shown to decrease toxic huntingtin protein levels. In one embodiment, the disclosed compounds and methods can be used to remove excess copper from subject having a neurological disease in order to treat or reduce symptoms of the disease.

One embodiment of the present invention provides a method for the treatment of neurological disease by administering to a subject one or more of the disclosed compounds according to Formula I, II, III, IV, V, VI, VII or an enantiomer, polymorph, or pharmaceutically acceptable salt thereof, in an amount effective to reduce labile copper concentration in subjects in need thereof. In such an embodiment, the disclosed compounds bind to labile copper to form a compound-copper complex that is excreted from the body. Reducing labile copper concentrations in brain tissue, cerebrospinal fluid, or in the circulation can reduce oxidative stress and the formation of Lewy bodies in subjects with Parkinson's disease, or reduce the expression of huntingtin protein in subjects with Huntington's disease. Neurological conditions that can be treated or prevented using the disclosed compounds include, but are not limited to, Alzheimer's disease, Parkinson's disease, and Huntington's disease.

4. Obesity

There are positive correlations of copper levels with BMI (Body Mass Index). This suggests that copper may be functionally linked to fat accumulation in obese patients. In one embodiment, reducing circulating levels of labile copper in the blood using the disclosed compounds and methods can prevent or reduce the progression of diabetes in a subject at risk thereof. In such an embodiment, the subject is administered one or more of the disclosed compounds in an amount effective to reduce the levels of circulating labile copper. The copper chelating compounds bind to labile copper, creating a compound-copper complex. The complex is excreted from the body, thus reducing the labile copper in circulation. In one embodiment reducing the levels of labile copper using the disclosed compounds can prevent or reduce the progression of diabetes in a subject.

5. Diabetes

Copper is involved in oxidative stress which is associated with the progression of diabetes mellitus. Patients with diabetes show higher plasma concentration levels of copper than healthy patients. In one embodiment, using the disclosed compounds and methods to reduce plasma copper levels in subjects with diabetes can slow down or halt the progression of diabetes.

One embodiment of the present invention provides a method for the treatment of diabetes by administering to a subject one of more of the disclosed compounds in an amount effective to reduce labile copper levels in the plasma by binding to labile copper. The bound compound-copper complex is excreted from the body, thus reducing the levels of labile copper in the plasma. By maintaining a healthy copper concentration, the symptoms and progression of diabetes can be slowed down or halted.

6. Cancer

An adequate supply of copper is not only critical for normal cell physiology but is also important in cancer progression. Increased copper levels have been shown to stimulate angiogenesis, the formation of new blood vessels from existing vasculature, presumably by influencing the activity of proangiogenic factors, including VEGF, bFGF, TGFβ, and angiogenin. High serum copper concentrations are associated with a variety of cancers including lymphoma, reticulum cell sarcoma, bronchogenic and laryngeal squamous cell carcinomas, cervical, breast, stomach, and lung cancers. Additionally, increased copper levels in these cancers have been linked to drug resistance. Many cancers, such as hairy cell leukemia, melanomas, thyroid cancers, colorectal cancers, and non-small cell lung cancer (NSCLC), are related to mutations in BRAF kinase. Copper has been shown to be critical in the BRAF signaling pathway. Decreasing copper levels has been shown to decrease tumor growth.

One embodiment of the present invention provides a method for the treatment of cancer by administering to a subject an effective amount of the disclosed compounds according to Formula I, II, III, IV, V, VI, VII, or an enantiomer, polymorph, or pharmaceutically acceptable salt thereof, or a pharmaceutical composition including the compounds according to Formula I, II, III, IV, V, VI, VII, or an enantiomer, polymorph, or pharmaceutically acceptable salt thereof to remove copper from the tumor microenvironment or out of circulation to reduce angiogenesis and tumor growth. In such an embodiment, labile copper in the tumor microenvironment or blood circulation is reduced, and the chelating compound-copper complex is excreted from the body. Reducing copper levels in tumors or in the blood of subjects with cancer can reduce angiogenesis and tumor growth. In some embodiments, the chelating compounds are conjugated with moieties that can bind to tumor specific antigens, thus ensuring the chelators are delivered to the appropriate tissue. Cancers to be treated by the disclosed compositions include, but are not limited to, lymphoma, reticulum cell sarcoma, bronchogenic and laryngeal squamous cell carcinomas, cervical, breast, stomach, lung cancers, hairy cell leukemia, melanomas, thyroid cancers, colorectal cancers, and non-small cell lung cancer (NSCLC).

EXAMPLES

Example 1: Synthesis of phenPS and naphPS (Shown in Scheme 1)

Scheme 1

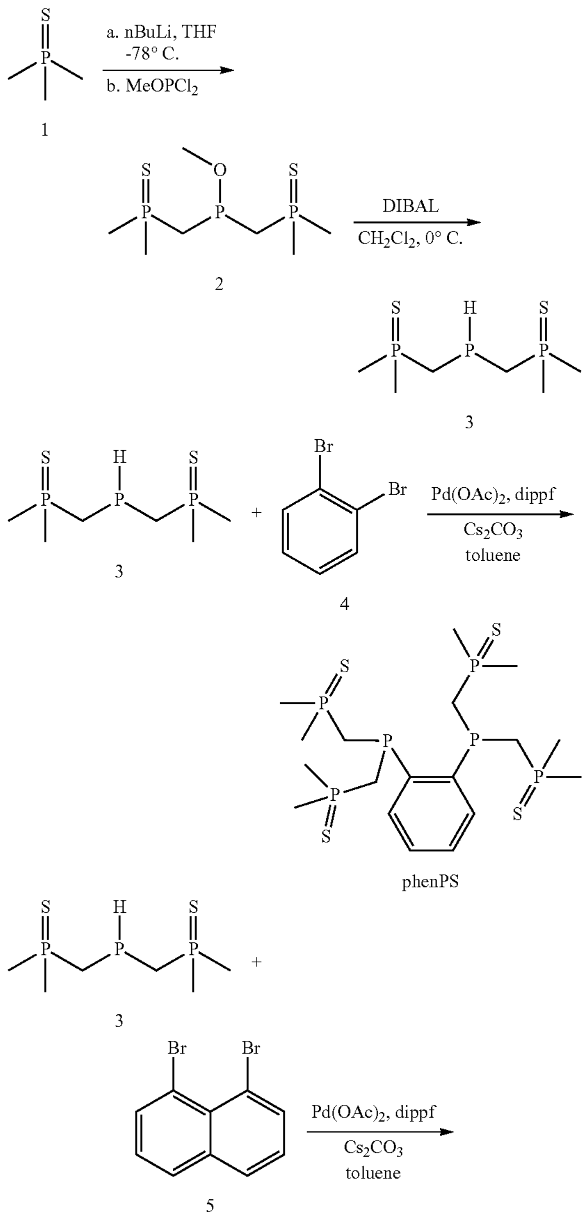

-continued

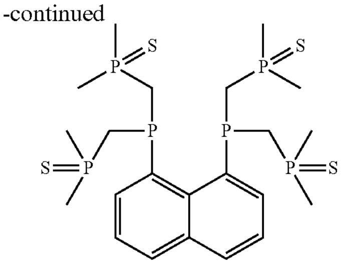

naphPS

Materials and Methods

Trimethylphosphine (25 g SureSeal bottle) and 1,1'-bis (di-isopropylphosphino)ferrocene were purchased from Sigma-Aldrich, $Pd(OAc)_2$ was purchased from Ark Pharm, Inc., and all other reagents were obtained from standard commercial sources. $[Cu(I)MCL-2]PF_6$ was prepared as previously reported (Bagchi, P., et al., *J. Am. Chem. Soc.,* 135(49) (2013)). PIPES buffer was prepared from piperazine-N,N'-bis(2-ethanesulfonic acid) (GFS Chemicals) and volumetric standard KOH (Fluka). NMR: $^{1}H$ (400 MHz) and $^{31}P$ (161 MHz) spectra were recorded at ambient temperature on a Varian Mercury 400 instrument unless specified otherwise. $^{1}H$ NMR spectra at 500 MHz were recorded at 25° C. or 80° C. on a Bruker Avance IIIHD 500, while $^{13}C$ spectra at 176 MHz were recorded at 25° C. on a Bruker Avance IIIHD 700. $^{1}H$ and $^{13}C$ chemical shifts are reported relative to internal TMS and $^{31}P$ shifts in ppm relative to 85% $D_3PO_4$ in an internal sealed capillary. EI-MS: selected peaks, m/z (intensity).

Methyl bis(dimethylphosphorothioylmethyl)phosphinite (2). A 250 mL 2-necked flask equipped with stir bar, rubber septum, and bubbler was flushed with argon and charged with anhydrous diethyl ether (100 mL) and diethyl chlorophosphite (2.00 g, 15.0 mmol, weighed within a syringe). The mixture was cooled to −78° C. A separate 100 mL flask containing a stir bar was charged with trimethylphosphine sulfide, sealed, and flushed with argon. TMEDA (4.5 mL, 30 mmol) and THE (~70 mL) were added under stirring, and the resulting solution was cooled to −78° C. to give a white suspension. Butyllithium solution (2.5 M in hexane, 12 mL, 30 mmol) was added dropwise under rapid stirring, resulting in a clear homogeneous solution upon complete addition. This solution was transferred via cannula to the rapidly stirred methyl dichlorophosphite solution. A white precipitate formed immediately. After 30 min, the cooling bath was removed and butanone (1 mL) was added to quench any residual organolithium species. The mixture was diluted with dry $Et_2O$ to 250 mL, and the solid was collected by filtration under argon pressure (chromatography column), washed with $Et_2O$, redissolved in dichloromethane, and filtered. The filtrate was concentrated to dryness, and the residue was recrystallized by dissolution in hot methanol (25 mL) followed by cooling to 4° C. under argon. The resulting colorless crystalline powder was collected by filtration under argon pressure, washed with a small amount of cold methanol, and dried under high vacuum at 60° C. Yield 1.96 g (7.09 mmol, 47%). $^{1}H$ NMR ($CDCl_3$, 400 MHz) δ 1.86 (d, J=13.0 Hz, 6H), 1.89 (d, J=12.9 Hz, 6H), 2.53 (dd, $^{2}J_{P(S)-H}$=14.1 Hz, $^{2}J_{H-H}$=11.9 Hz, 2H), 2.74 (apparent td, $^{2}J_{P(S)-H}$≈$^{2}J_{H-H}$≈13.7 Hz, $^{2}J_{P-H}$=5.2 Hz, 2H), 3.65 (d, J=14.0 Hz, 2H). $^{13}C\{^{1}H\}$ NMR ($CDCl_3$, 176 MHz) δ 22.8 (dd, $J_{PC}$=56.2, 3.7 Hz), 23.3 (dd, $J_{PC}$=55.7, 2.2 Hz), 40.6 (ddd, $J_{PC}$=48.7, 38.0, 9.6 Hz), 57.7 (d, $J_{PC}$=19.4 Hz).

$^{31}P\{1H\}$ NMR ($CDCl_3$, 161 MHz) δ 119.0 (t, J=58.7 Hz), 32.5 (d, J=58.7 Hz). EI-MS m/z 276 (M+, 20), 261 (30), 169 (100), 93 (40), 75 (85), 61 (30). EI-HRMS calcd for $M^+$ $C_7H_{19}OP_3S_2$ 276.0091, found 276.0090.

Bis(dimethylphosphorothioyl)phosphine (3). Phosphinite 2 (1.76 g, 6.37 mmol) was stirred in anhydrous DCM (35 mL) under argon. The resulting suspension was cooled in an ice bath, and diisobutylaluminum hydride solution (25% in hexane, ~1.2 M, 7.8 mL, 1.5 molar equiv.) was added in small portions over a period of 10 minutes. The resulting clear solution was stirred for 30 minutes at 0° C. followed by 1 hour at room temperature. The resulting mixture was carefully poured into a rapidly stirred solution of citric acid (2.5 g, 2 molar equiv.) in water (10 mL) within a 125 mL Erlenmeyer flask (Caution: exothermic process with gas evolution). The mixture was rinsed in completely with a further 10 mL of DCM and 1 M citrate buffer (20 mL, pH ~5.5) was added. The organic layer was collected, and the aqueous layer was extracted with DCM (2×10 mL). The combined organic phases were dried with anhydrous $Na_2SO_4$, diluted with cyclohexane (40 mL) and concentrated under reduced pressure to give a crystalline slurry. The mixture was further diluted with cyclohexane and concentrated again to remove residual DCM. The resulting material was collected by filtration, dried under nitrogen flow, and recrystallized from boiling water (15 mL) under argon to give the pure secondary phosphine as colorless granules. Yield 958 mg (3.89 mmol, 61%). $^1H$ NMR ($CDCl_3$, 400 MHz) δ 1.84 (d, J=12.8 Hz, 6H), 1.86 (d, J=12.8 Hz, 6H), 2.43-2.58 (m, 4H), 3.99 (dtp, J=214.7, 18.2, 6.8 Hz, 1H). $^{13}C\{^1H\}$ NMR (176 MHz, $CDCl_3$) δ 22.17 (dd, JPC=55.7, 2.2 Hz), 22.33 (dd, JPC=55.6, 2.6 Hz), 26.3 (ddd, JPC=47.5, 25.9, 6.7 Hz). $^{31}P\{1H\}$ NMR ($CDCl_3$, 161 MHz) δ −101.5 (t, J=41.3 Hz), 37.15 (d, J=41.3 Hz). EI-MS m/z 246 ($M^+$, 43), 153 (33), 139 (49), 138 (40), 93 (57), 75 (100), 61 (19). EI-HRMS calcd for $M^+$ $C_6H_{17}P_3S_2$ 245.9985, found 245.9985. In a larger scale batch, the phosphinite intermediate 2 was prepared as described above from methyl dichlorophosphite (3.27 g, 24.6 mmol) and trimethylphosphine sulfide (5.32 g, mmol) but with omission of the recrystallization step, yielding 4.75 g (70%) of crude material. After reducing a portion of this material (2.15 g) with DIBAL overnight, the product was purified by column chromatography on silica gel (DCM-MTBE) in lieu of the recrystallization steps to give phosphine 3 as a colorless solid. Yield 1.22 g (64%).

1,2-Bis(bis(dimethylphosphorothioylmethyl)phosphino) benzene; (phenPS). A 25 mL round bottom flask containing a stir bar was charged with secondary phosphine 3 (315 mg, 1.28 mmol), $Cs_2CO_3$ (350 mg, 1.07 mmol), $Pd(OAc)_2$ (10.0 mg, 0.045 mmol), and dippf (20.0 mg, 0.0478 mmol). The flask was capped with a rubber septum and flushed with argon for 10 min. Toluene (9.0 mL) was added, followed by 1,2-dibromobenzene (59 μL, 115.4 mg, 0.489 mmol). The septum was replaced with a condenser connected to an argon line and bubbler, and the mixture was stirred at reflux under argon for 20 h. After cooling to room temperature, the mixture was diluted with saturated aqueous $NaHCO_3$ and extracted using DCM (3×10 mL). The combined organic layers were dried over $Na_2SO_4$, filtered, and concentrated by rotary evaporation, and the residue was separated by column chromatography on silica gel using DCM-MTBE (5:1) to afford 125 mg (0.221 mmol, 45% yield) of the product as a white solid. For further purification, the solid was dissolved under stirring in boiling DCM (2.0 mL) and diluted slowly with MTBE (1.0 mL) as DCM was boiled away to give a crystalline slurry. After cooling to room temperature, the product was collected by filtration and dried under argon flow to give a colorless crystalline powder. $^1H$ NMR ($CDCl_3$, 400 MHz) δ 1.88 (d, J=12.8 Hz, 12H), 1.96 (d, J=13.0 Hz, 12H), 2.75 (dd, J=13.9, 10.7 Hz, 4H), 3.06 (dd, J=13.9, 12.0 Hz, 4H), 7.43-7.47 (m, 2H), 7.58-7.64 (m, 2H). $^1H$ NMR (DMSO, 500 MHz, 25° C.) δ 1.70 (d, J=13.1 Hz, 12H), 1.80 (d, J=13.2 Hz, 12H), 2.86 (dd, J=14.2, 10.6 Hz, 12H), 2.98 (apparent t, $^2J_{PH}\approx{}^2J_{HH}\approx14$ Hz, 4H), 7.43-7.48 (m, 2H), 7.79-7.84 (m, 2H). $^{13}C\{^1H\}$ NMR (176 MHz, $CDCl_3$) δ 22.72 (d, $J_{PC}$=55.6 Hz), 23.09 (d, $J_{PC}$=55.9 Hz), 33.05 (m), 130.2, 130.77 (t, $J_{PC}$~2.1 Hz), 143.12-143.35 (m). $^{31}P\{^1H\}$ NMR ($CDCl_3$, 161 MHz) δ −53.01 (symmetric m, 2 P), 36.84 (symmetric m, 4 P). MS (ESI) m/z 567 ($[M+H]^+$, 100%); ESI-HRMS calcd for $C_{18}H_{37}P_6S_4$ ($[M+H]^+$) 567.0198, found 567.0187.

1,8-Bis(bis(dimethylphosphorothioylmethyl)phosphino) naphthalene; (naphPS). A 25 mL round bottom flask was charged with 1,8-dibromonaphthalene (100.0 mg, 0.350 mmol), secondary phosphine 3 (207.2 mg, 0.841 mmol), $Cs_2CO_3$ (240 mg, 0.738 mmol), $Pd(OAc)_2$ (11.8 mg, 0.053 mmol, and dippf (27.0 mg, 0.064 mmol). The reaction and workup were conducted exactly as described for PhenPS except that the reflux time was 18 hours. Separation by column chromatography on silica gel using DCM:MTBE (3:1) furnished 70.6 mg (0.114 mmol, 33% yield) of the product as a green solid. Further purification by the method described for phenPS gave a yellow crystalline powder. $^1H$ NMR ($CDCl_3$, 400 MHz) δ 1.62 (d, J=12.8 Hz, 12H), 1.76 (d, J=12.8 Hz, 12H), 2.95-3.03 (m, 4H), 3.48 (apparent t, $^2J_{PH}\approx{}^2J_{HH}\approx13.5$ Hz, 4H), 7.57 (t, J=7.6 Hz, 2H), 7.90 (d, J=8.1 Hz, 2H), 8.22 (d, J=6.5 Hz, 2H). $^1H$ NMR (DMSO, 500 MHz, 25° C.) δ 1.50 (d, J=13.1 Hz, 12H), 1.54 (d, J=13.1 Hz, 12H), 3.04-3.11 (m, 4H), 3.31 (apparent t, $^2J_{PH}\approx{}^2J_{HH}$~14.4 Hz, 4H), 7.61 (dd, J=7.9, 7.2 Hz, 2H), 8.00-8.02 (m, 2H), 8.32-8.35 (m, 2H). $^{13}C\{^1H\}$ NMR (176 MHz, $CDCl_3$) δ 23.17 (d, $J_{PC}$=54.6 Hz), 24.18 (d, $J_{PC}$=55.4 Hz), 34.9 (m), 125.87, 131.92, 133.94 (t, $J_{PC}$=6.8 Hz), 135.54 (m), 135.59, 140.27 (t, $J_{PC}$=26.1 Hz). $^{31}P\{^1H\}$ NMR ($CDCl_3$, 161 MHz) δ −46.99 (symmetric m, 2 P), 36.12 (symmetric m, 4 P). ESI m/z 617.03 [M+H]+. $ESI^+$-HRMSM $[M+H]^+$ calcd for $C_{22}H_{38}P_6S_4$ 617.0355, found 617.0355.

Example 2: Synthesis of phenPS-Cu(I) Complex and naphPS-Cu(I) Complex

Materials and Methods phenPS-Cu(I) Complex; $[Cu(I)phenPS]BF_4$. To a solution of phenPS (30.0 mg, 53 μmol) in DCM (0.4 mL) was added a solution of $[Cu(CH_3CN)_4]BF_4$ (20.0 mg, 63.5 μmol) in $CH_3CN$ (0.4 mL). The solvent was slowly evaporated under a stream of argon until colorless crystals started to form. After the solution was allowed to stand for 2 hours, the crystals were collected by filtration, rinsed with DCM, and dried overnight (high vacuum). Yield: 27.8 mg (38.7 μmol, 73%). $^1H$ NMR (DMSO-$d_6$, 500 MHz, 80° C.) δ 1.78 (d, J=13.4 Hz, 12H), 1.92 (d, J=13.3 Hz, 12H), 3.08-3.15 (m, 4H), 3.27-3.34 (m, 4H), 7.64-7.68 (m, 2H), 8.05-8.11 (m, 2H). $^{31}P\{^1H\}$ NMR (DMSO-$d_6$, 202 MHz) δ −32.53 (symmetric broad, 2 P), 44.62 (symmetric sharp, 4 P).

naphPS-Cu(I) Complex; $[Cu(I)naphPS]BF_4$. To a solution of naphPS (20.0 mg, 32 μmol) in DCM (0.4 mL) was added a solution of $[Cu(CH_3CN)_4]BF_4$ (10.9 mg, 35 μmol) in $CH_3CN$ (0.4 mL). The solvent was slowly evaporated under a stream of argon until yellow crystals started to form. After the solution was allowed to stand for 2 hours, the crystals were collected by filtration, rinsed with DCM, and dried overnight (high vacuum). Yield: 24.2 mg (31.5 μmol, 81%). $^{1}H$ NMR ($DMSO-d_6$, 500 MHz, 80° C.) δ 1.66 (d, J=13.4 Hz, 12H), 1.83 (d, J=13.3 Hz, 12H), 3.19-3.25 (m, 4H), 3.31-3.37 (m, 4H), 7.67 (dd, J=8.0, 7.2 Hz, 2H), 8.15 (apparent dq, J=8.3, 1.4 Hz, 2H), 8.37-8.41 (m, 2H). $^{31}P\{^{1}H\}$ NMR ($DMSO-d_6$, 202 MHz) δ −34.47 (symmetric broad, 2 P), 42.30 (symmetric sharp, 4 P).

Example 3: Crystallography of Ligands and Cu(I)—Complexes

Materials and Methods

Single crystals were obtained by diffusing with MTBE into a saturated solution of each ligand in dichloromethane. The corresponding Cu(I) complexes, [CU(I)phenPS]$BF_4$ and [Cu(I)naphPS]$BF_4$ were isolated from a mixture of dichloromethane and acetonitrile (1:1) containing equimolar amounts of [$Cu(CH_3CN)_4$]$BF_4$ and ligand.

Results

Crystal structures of Cu(I) complexes, [CU(I)phenPS] $BF_4$ and [Cu(I)naphPS]$BF_4$ are shown in FIG. 2.

Example 4: Molar Ratio Titration of PhenPS and NaphPS Against BCA Copper(I) Complex Materials and Methods In a quartz cuvette with 1 cm path length, BCA (9.0 μL) was diluted from a 50 mM aqueous stock solution (dissolved by addition of KOH) into 3.0 mL of buffer (10 mM PIPES, 0.1 M KCl, pH 7.0, 25° C.). Furthermore, Cu(II)$SO_4$ (5.0 μL) from a 30 mM stock solution) and sodium ascorbate (7.5 μL from a 60 mM stock solution) were added. After equilibration for 10 minutes, a UV-vis spectrum was recorded, and the solution was titrated in 1-10 μL aliquots with a 3 mM stock solution of phenPS in DMF or naphPS in DMSO. For phenPS, the endpoint occurred at 1.04 molar equivalents on the basis of the mass employed for stock solution preparation, consistent with incomplete removal of the solvent of crystallization as observed by $^{1}H$ NMR. An independent molar ratio titration against [Cu(I)MCL-2]$PF_6$ confirmed the stock concentration as 2.88 mM rather than 3.0 mM, and the plotted Cu(I)/phenPS ratio is adjusted accordingly.

Results

Figures 6A, 6B:
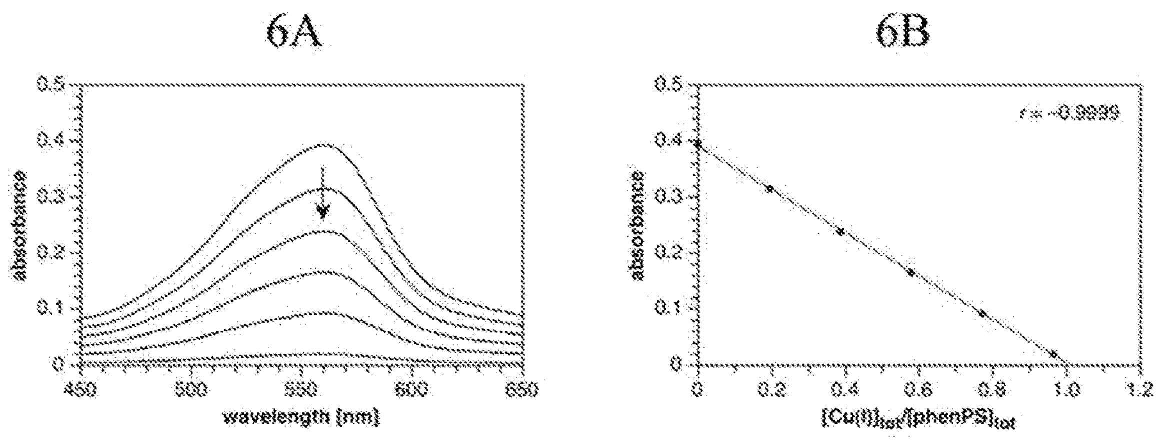
FIG. 6A is a representative UV-vis absorption spectrum to determine the Cu(I) binding stoichiometry of phenPS using BCA as an indicator. A solution of Cu(I) 50 (μM) in the presence of excess BCA (150 μM) was titrated with 0.2 molar equiv. aliquots of phenPS at pH 7.0 (10 mM PIPES, 0.1 M KCl, 25° C.).
FIG. 6B is a representative linear regression for the absorbance at 562 nm vs. the ratio of total Cu(I) and phenPS concentration.
Figures 7A, 7B:
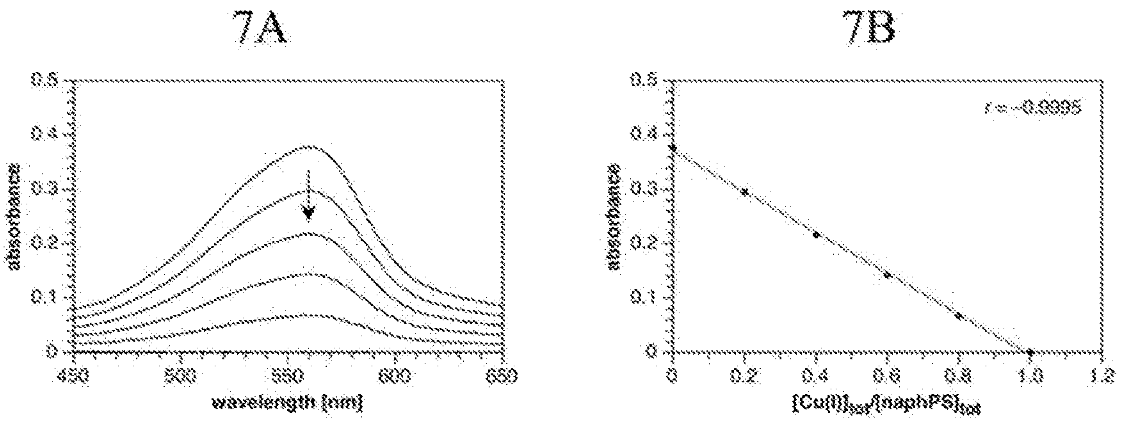
FIG. 7A is a representative UV-vis absorption spectrum to determine the Cu(I) binding stoichiometry of naphPS using BCA as an indicator. A solution of Cu(I) 50 (μM) in the presence of excess BCA (150 μM) was titrated with 0.2 molar equiv. aliquots of phenPS at pH 7.0 (10 mM PIPES, 0.1 M KCl, 25° C.).
FIG. 7B is a representative linear regression for the absorbance at 562 nm vs. the ratio of total Cu(I) and naphPS concentration.

The spectrophotographic results are shown in FIG. 6 and FIG. 7 for phenPS and naphPS, respectively. The titration yielded a linear decrease in absorbance at 562 nm, indicating quantitative removal of Cu(I) by both ligands. This is consistent with a 1:1 complex stoichiometry.

Example 5: Molar Ratio Titration of PhenPS and NaphPS with [Cu(I)MCL-2]$PF_6$ Materials and Methods In a quartz cuvette with 1 cm path-length, a 50 μM aqueous solution of phenPS was prepared by diluting the ligand from a stock solution (3 mM in DMF) into 2.95 mL of aqueous buffer (10 mM PIPES, 0.1 M KCl, pH 7) under rapid stirring. After recording a UV-vis absorption spectrum from 240 to 500 nm, [Cu(I)MCL-2]$PF_6$ (3 mM stock solution in water) was added in 5 μM aliquots up to 95 μM. The absorption spectrum was recorded after a 1 min mixing period following each aliquot. To derive an accurate reference spectrum of Cu(I)-MCL-2 complex, a separate titration was conducted using pure DMF in place of the phenPS stock solution. The exact concentration of the phenPS stock solution was calibrated against [Cu(I)MCL-2]$PF_6$ by plotting the apparent fractional saturation of the ligand, calculated as $f=(A-A_0)/(A_{sat}-A_0)$ where A corresponds to the absorbance at 290 nm and the subscripts 0 and sat refer to the spectra at 0 and 50 μM Cu(I), versus nominal molar equivalents of Cu(I) for the first 10 data points (0-0.9 molar equivalents). After concentration correction and subtraction of the DMF background absorption, non-linear least-squares fitting of the titration dataset over the wavelength range 250-400 nm was performed using a fixed log $\beta_{11}$ of 21.2 for Cu(I)-phenPS to yield a log $\beta_{12}$=31.86±0.07 (log $K_2$=10.66±0.07) for $Cu(I)_2$phenPS.

Results

Figures 8A, 8B:
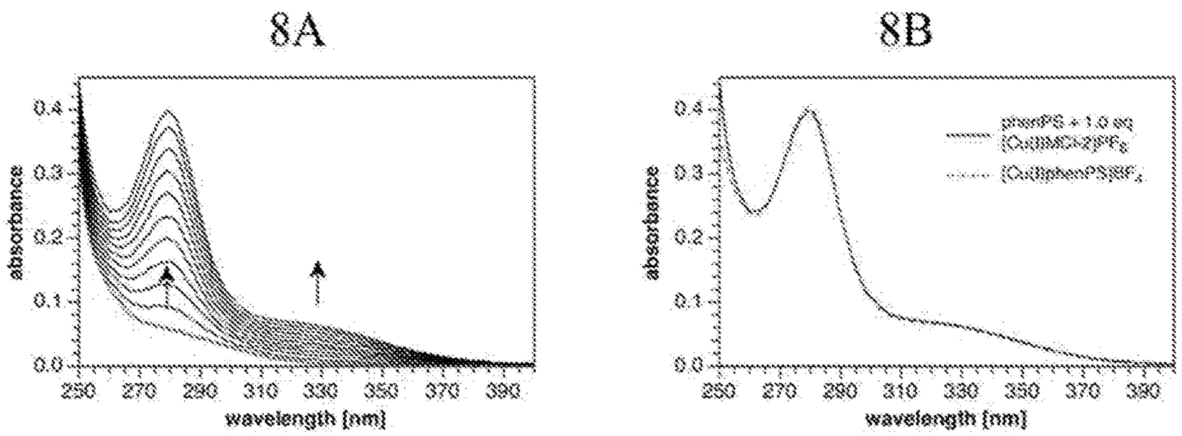
FIG. 8A is a representative UV-vis spectrum for 0.1 molar equiv. trace to determine molar ratio titration of phenPS with $[Cu(I)MCL\text{-}2]PF_6$ at pH 7.0 (10 mM PIPES, 0.1 M KCl, 25° C.). UV-vis traces for 0.1 molar equiv. aliquots of $[Cu(I)MCL\text{-}2]PF_6$. The red trace indicates the spectrum of phenPS alone.
FIG. 8B is an overlay for the UV-vis spectra of recrystallized $[Cu(I)phenPS]BF_4$ and a solution containing a 1:1 ratio of naphPS and $[Cu(I)MCL\text{-}2]PF_6$.
Figures 9A, 9B:
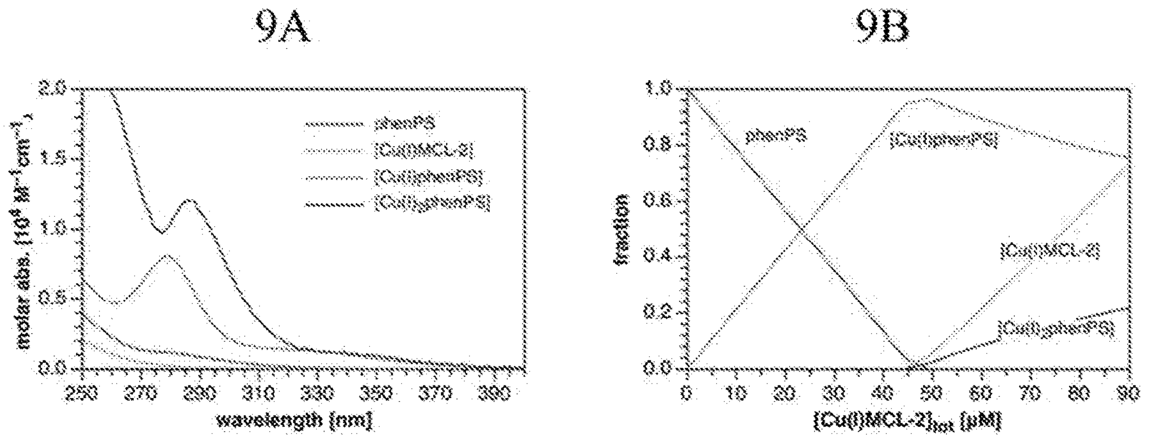
FIG. 9A is a representative deconvoluted UV-vis spectra to determine molar ratio titration of phenPS with $[Cu(I)MCL\text{-}2]PF_6$ at pH 7.0 (10 mM PIPES, 0.1 M KCl, 25° C.).
FIG. 9B is a species distribution diagram as a function of total [Cu(I)MCL-2] concentration. The concentration of each species is shown as a fraction of the total phenPS concentration.
Figures 10A, 10B:
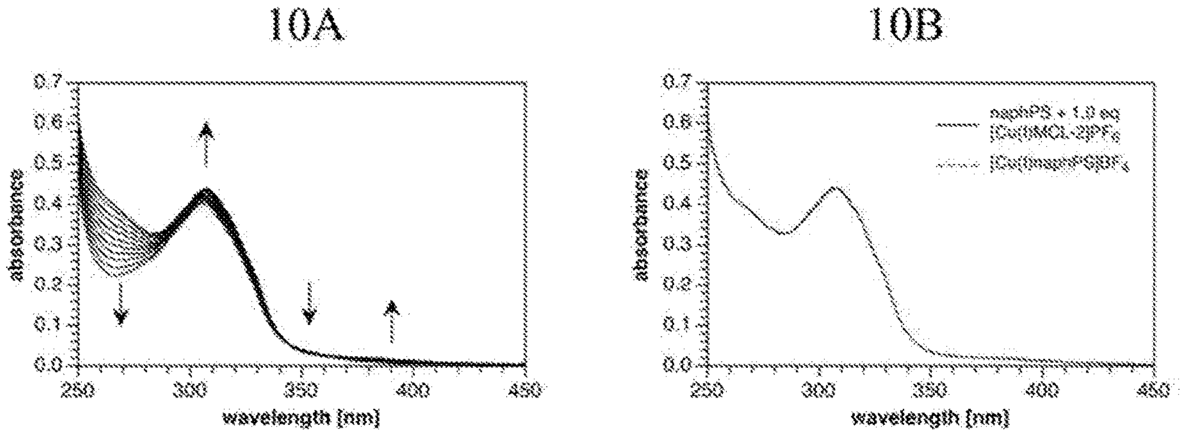
FIG. 10A shows the UV-vis traces for the titration of phenPS with 0.1 molar equiv. aliquots of $[Cu(I)MCL\text{-}2]PF_6$. The red trace indicates the spectrum of naphPS alone.
FIG. 10B is an overlay for the UV-vis spectra of recrystallized $[Cu(I)naphPS]BF_4$ and a solution containing a 1:1 ratio of naphPS and $[Cu(I)MCL\text{-}2]PF_6$.
Figures 11A, 11B:
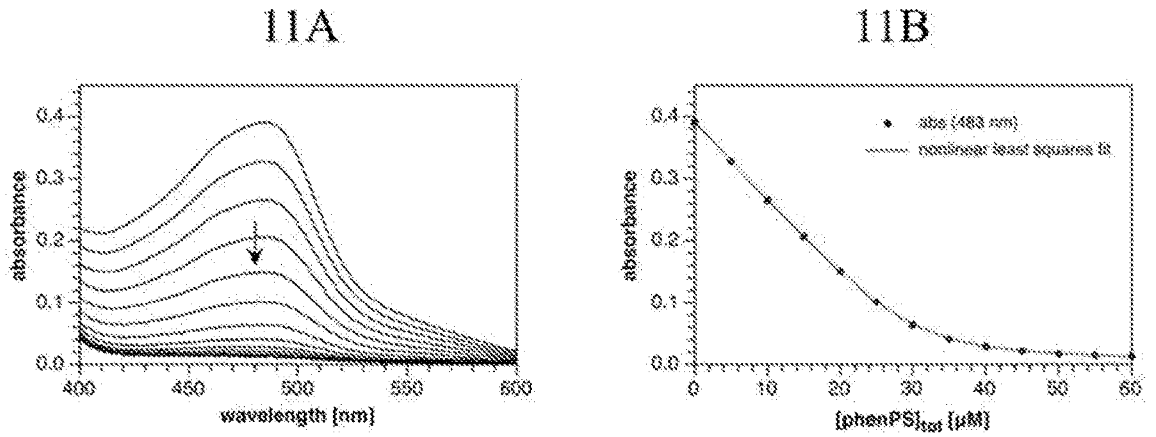
FIG. 11A shows representative UV-vis spectra used for determination of the 1:1 Cu(I) complex stability constant of phenPS in aqueous buffer at pH 7.0 (10 mM PIPES, 0.1 M KCl, 25° C.).
FIG. 11B is the nonlinear least squares fit at 483 nm.
Figures 12A, 12B:
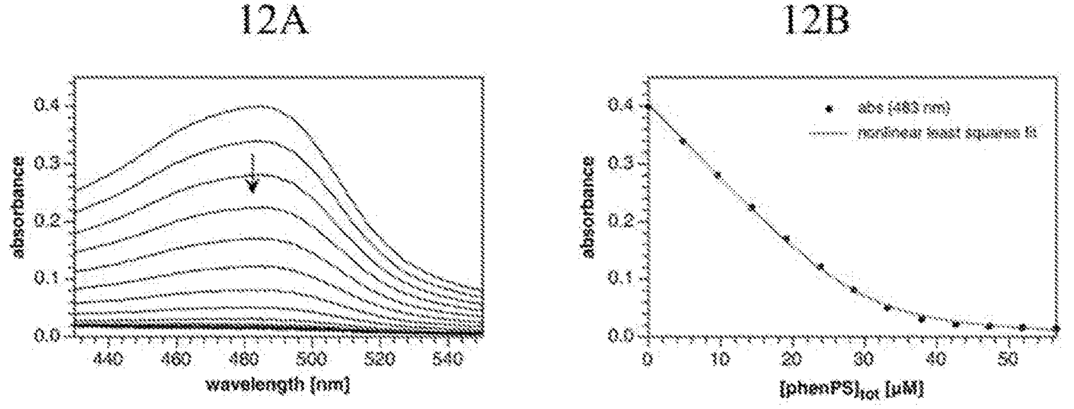
FIG. 12A shows representative UV-vis spectra used for determination of the Cu(I) stability constant of [(Cu(Ligand-2)], left, and [(Cu(Ligand-2)], right in aqueous buffer at pH 7.0 (10 mM PIPES, 0.1 M KCl, 25° C.).
FIG. 12B is the nonlinear least squares fit at 483 nm.

Consistent with a strong Cu(I)-ligand interaction, the UV-vis titration of phenPS with [Cu(I)MCL-2]$PF_6$ produced a linear increase of the absorption maximum up to a 1:1 Cu(I)-phenPS ratio, shown in FIG. 4A. The resulting spectrum is identical to that of isolated [Cu(I)phenPS]$BF_4$, FIG. 8. The calculated species distribution diagram, shown in FIG. 9, indicates that a significant portion of Cu(I) remains bound to MCL-2. As such, the affinity of MCL-2 is well matched for determining the log $K_2$ of phenPS through a ligand competition titration.

Example 6: Spectrophotometric Cu(I) Competition Titration Against BCS

Materials and Methods

An aqueous sodium bathocuproine disulfonate (BCS, Acros Organics) stock solution (60 mM) was prepared calibrated by competition titration against MCL-1 as previously described (Bagchi, P., et al., *J. Am. Chem. Soc.,* 135(49) (2013)). BCS (1.50 mM), sodium ascorbate (150 μM) and $CuSO_4$ (30 μM) were sequentially added via aqueous stock solutions to 3 mL of buffer (10 mM PIPES, 0.1 M KCl, pH 7.0) in a 1-cm path length cuvette equipped with magnetic stirring, and a UV-Vis absorption spectrum was recorded from 650-380 nm. PhenPS was added in 5 μM aliquots from a 2.88 mM stock solution in DMF and an absorption spectrum was acquired after a 2 min equilibration period following each aliquot. The titration was conducted in duplicate, and each dataset was analyzed by nonlinear least squares fitting over the spectral range from 650-400 nm using the Specfit software package from Spectrum Software Associates. The stability constant for naphPS was determined similarly except that the ligand was delivered from a 3.0 mM stock solution in DMSO and a 5-minute equilibration period was required to obtain a stable spectrum after each aliquot.

Results

Spectrophotometric titration of 30 μM Cu(I) with phenPS in the presence of excess BCS resulted in a gradual decrease of the absorption band centered at 483 nm, as shown in FIG. 4B. Non-linear least square fitting from 400-650 nm yielded a log K of 21.21±0.09 at pH 7.0 (10 mM PIPES, 0.1 M KCl, 25° C.), corresponding to a dissociation constant of $K_d$=0.6 zM, shown in FIG. 4C.

Example 7: Two-Photon Emission Ratiometric Imaging of Labile Cellular Cu(I)

Materials and Methods

Cells were grown on glass bottom culture dishes (MatTek) to 70% confluency in DMEM supplemented with 10% FBS and Penicillin/Streptomycin. Fresh growth medium supplemented with 50 μM $CuCl_2$ was supplied 21-24 hours prior to imaging. Before imaging, the media was replaced with pre-warmed DMEM without phenol red supplemented with 10% FBS, penicillin/streptomycin, and 100 mM sodium pyruvate containing 1 μM of crisp-17 and incubated at 37° C. in 5% $CO_2$ for 20 minutes. Cells were imaged at 37° C. under a humidified 5% $CO_2$ atmosphere using a Zeiss LSM confocal NLO 710 microscope equipped with a femtosecond pulsed Ti:sapphire laser. Scanning fluorescence micrographs were acquired with excitation at 880 nm and emission simultaneously collected over two channels with bandpass ranges of 479-536 and 611-750 nm. After imaging under basal conditions, intracellular copper levels were increased by addition of CuGTSM, or an oxidative stress response was stimulated by exposure to a buffer solution containing 100 μM 2,2'-dithiodipyridine (DTDP). The quantitative image analysis software package, ImageJ, was used to analyze the change in the fluorescence emission ratio and fractional saturation of crisp-17 over time as described previously for chromis-1. The emission ratio for the region of interest was averaged at each time point.

Results

Figures 13A, 13R:
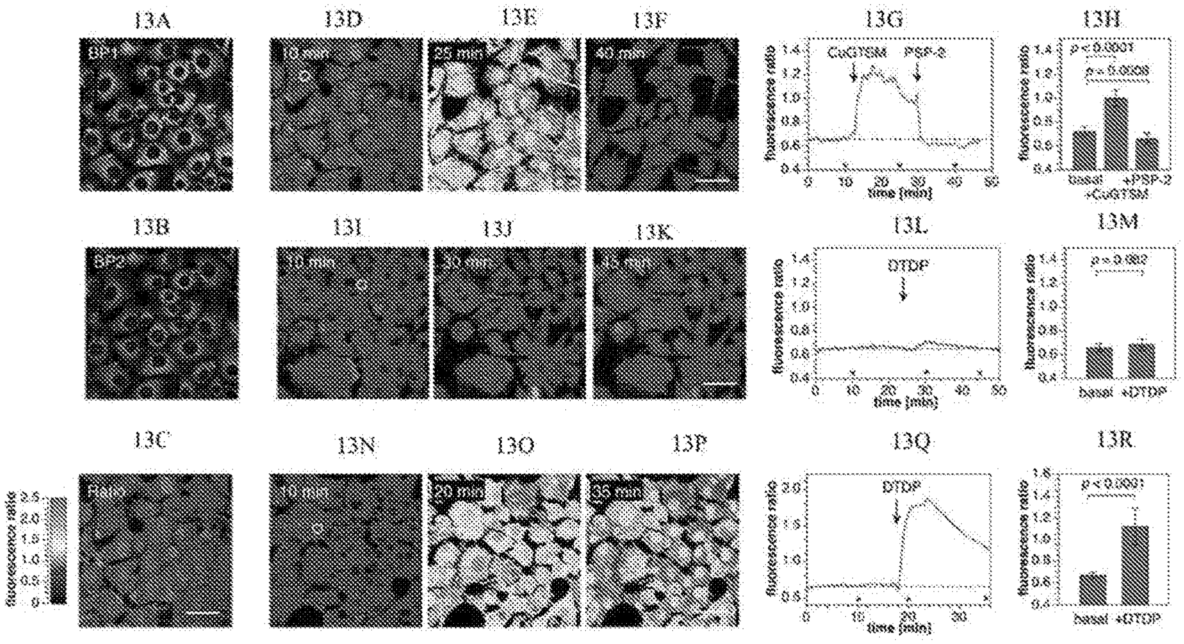
FIG. 13A is a fluorescence intensity image acquired with emission channels of 479-536 nm (BP1).
FIG. 13R is the mean fluorescence ratio of the cytoplasmic region averaged over 20 cells (P values calculated for n=20 using a two-tailed test).

FIGS. 13A-13C show that the copper ligand readily enters cells and produces bright fluorescence staining. The corresponding intensity ratio image, FIG. 13C produced a relatively uniform ratio distribution of 0.73±0.2. FIG. 13D-13H show that when cells are exposed to CuGTSM the cytoplasmic intensity ratio dramatically increased from 0.72±0.4 to ~1.00±0.7. FIGS. 13I-13M show that the copper ligand showed a small statistically non-significant increase of the fluorescence ratio upon addition of DTDP. However, FIGS. 13N-13R show that when growing cells on a medium supplemented with 50 μM $CuCl_2$ for one week produced a dramatic increase in the average ratio, consistent with DTDP-induced release of sulfhydryl-bound Cu(I).

Example 8: Synthesis of Agarose-Conjugated phenPS (phenPS-Agarose)

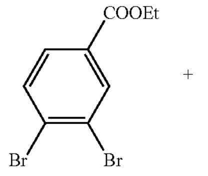

6

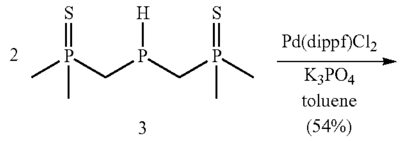

3

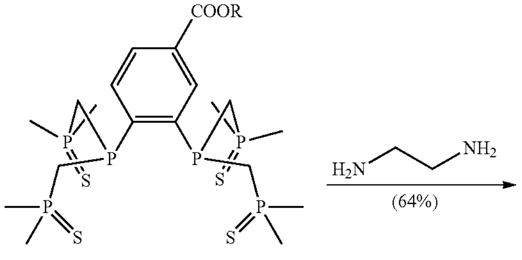

7a R = Et phenPS-$CO_2$Et
7b R = H phenPS-$CO_2$H

-continued

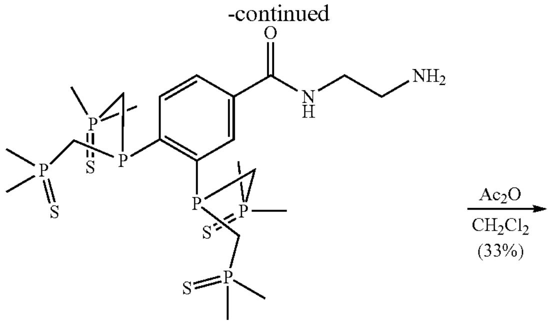

8
phenPS-$NH_2$

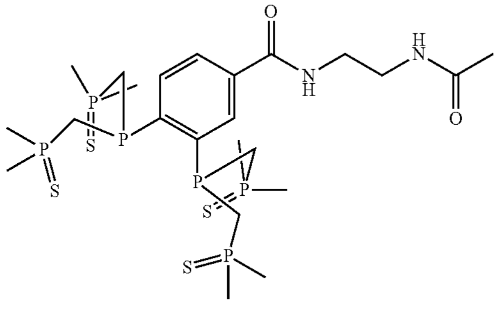

9
phenPS-NHAc

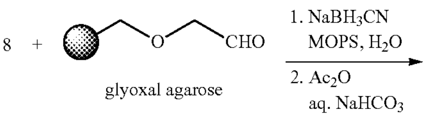

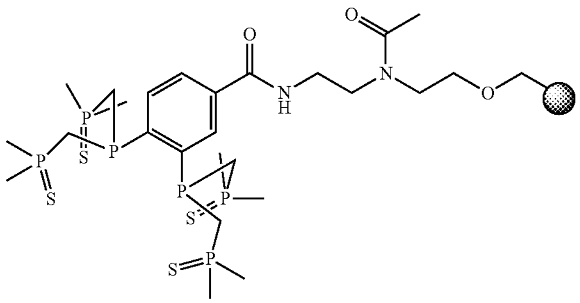

10
phenPS-agarose

Ethyl 3,4-dibromobenzoate (6). A mixture of 3,4-dibromobenzoic acid (500 mg, 1.79 mmol), conc. sulfuric acid (0.2 mL, 2 equiv.) and ethanol (10 mL) was refluxed overnight. After cooling, the mixture was poured onto saturated aq. $Na_2CO_3$ (5 mL) and concentrated under reduced pressure. The residue was diluted with water (10 mL) and extracted 3-times with $CH_2Cl_2$. The combined extracts were dried with $Na_2SO_4$ and concentrated to give a brown oil which solidified on standing. Yield 462 mg (1.65 mmol, 84%). $^1$H NMR ($CDCl_3$, 400 MHz) δ 1.40 (t, J=7.1 Hz, 3H), 4.38 (q, J=7.1 Hz, 2H), 7.70 (d, J=8.3 Hz, 1H), 7.82 (dd, J=8.3, 2.0 Hz, 1H), 8.27 (d, J=2.0 Hz, 1H). $^{13}$C NMR ($CDCl_3$, 100 MHz) δ 14.2, 61.6, 125.0, 129.2, 130.2, 131.0, 133.7, 134.6, 164.7. EI-MS m/z 310 (40), 308 (65), 306 (M+, 40), 282 (50), 280 (75), 278 (50), 265 (70), 263 (100), 261 (70), 237 (25), 235 (50), 233 (25), 75 (65), 74 (55). EI-HRMS calcd for $M^+$ $C_9H_8Br_2O_2$ 305.8886, found 305.8893.

Ethyl 3,4-bis(bis(dimethylphosphorothioylmethyl)phosphino)benzoate (7a). A suspension of ethyl 3,4-dibromobenzoate (680 mg, 2.21 mmol), bis(dimethylphosphorothioylmethyl)phosphine (1.15 g, 2.1 equiv.), $K_3PO_4$ (1.42 g, 3 equiv.), Pd(dippf)$Cl_2$ (66 mg, 5 mol %) and toluene (42 mL) was deoxygenated by bubbling with argon for 15 min and then refluxed under argon with vigorous stirring for 3 days. After cooling, the mixture was poured into water and extracted with DCM. The combined organic layers were dried over $Na_2SO_4$, concentrated, and separated by column chromatography on silica gel (10:1 DCM-MTBE) to give the product as a beige solid. Yield 761 mg (1.19 mmol, 54%). An analytical sample was obtained as a colorless crystalline powder by recrystallization from boiling DCM-EtOH under argon. $^1$H NMR ($CDCl_3$, 400 MHz) δ 1.41 (t, J=7.1 Hz, 3H), 1.90 (d, J=12.8 Hz, 12H), 1.95 (d, J=13.0 Hz, 6H), 1.97 (d, J=13.0 Hz, 6H), 2.71-2.82 (m, 4H), 3.05-3.13 (m, 4H), 4.40 (q, J=7.1 Hz, 2H), 7.69 (dt, J=8.0, 3.7 Hz, 1H), 8.06 (dd, J=8.0, 1.6 Hz, 1H), 8.25 (dt, J=1.6, 3.7 Hz, 1H). Note: The triplet couplings of the signals at 7.69 and 8.25 can be attributed to virtual coupling of each proton to both phosphines, which have virtually identical chemical shifts given that the $AA'X_2X'_2$ splitting patterns observed in the $^{31}P\{^1H\}$ NMR spectrum of ester 7 are superimposable with those of fully symmetrical phenPS. The $^{31}P\{^1H\}$ NMR spectra of amides 8 and 9 reveal $ABX_2X'_2$ splitting patterns for the two phosphines, indicating that their chemical shifts, while not identical, are nevertheless extremely close, and virtual coupling is still observed in the corresponding $^1$H NMR spectra. $^{31}P\{^1H\}$ NMR ($CDCl_3$, 162 MHz) δ −52.9 (m, 2P), 36.9 (m, 4P). EI-MS m/z 638 ($M^+$, 5), 531 (80), 423 (40), 107 (30), 75 (100). EI-HRMS calcd for $M^+$ $C_{21}H_{40}O_2P_6S_4$ 638.0331, found 638.0334.

3,4-Bis(bis(dimethylphosphorothioylmethyl)phosphino)benzoic acid (7b) (Formula VI). A solution of ethyl ester 7a (0.19 g, 0.297 mmol) in DCM (2 mL) was combined with a 2 M solution of NaOH in methanol (0.446 mL). The mixture was stirred for 5.5 hours at room temperature and quenched with carbon dioxide (dry ice). The reaction mixture was concentrated under reduced pressure, and the solid residue was dissolved in water. After extraction with MTBE (2 times), the aqueous phase was purged with nitrogen gas, and a solution of 1 M HCl (1 mL) was added. The formed precipitate was filtered off, washed with water, and dried overnight (60° C./0.08 Torr). Yield (0.091 g, 50%). $^1$H NMR (400 MHz, $CDCl_3$) δ 8.31-8.26 (m, 1H), 8.01 (dd, J=8.0, 1.5 Hz, 1H), 7.73-7.66 (m, 1H), 3.11 (dd, J=21.3, 12.9 Hz, 4H), 2.86-2.73 (m, 4H), 1.94 (ddd, J=24.9, 12.9, 3.0 Hz, 24H). $^{31}$P NMR (162 MHz, $CDCl_3$) δ 37.97-36.46 (m),−52.44-54.27 (m). HR-MS (ESI−): m/z [$M^-$]: $C_{19}H_{35}O_2P_6S_4$: calculated: 608.9951, found 608.9951.

N-(2-Aminoethyl)-3,4-bis(bis(dimethylphosphorothioylmethyl)phosphino)benzamide (8). Ester 7a (336 mg, 526 μmol) was stirred in ethylenediamine (5 mL) under argon for 2 days at ambient temperature (20-23° C.). The solution was diluted slowly with water (15 mL) and the mixture was stirred in an ice bath for 1 hour. The precipitate was collected by filtration, transferred to a round bottom flask using methanol, and dried for 2 hours at 60° C./0.1 torr to give the product as a white solid containing a trace of impurity by $^1$H NMR. Yield 295 mg (64%). A portion of this material (230 mg, 352 μmol) was stirred with 3-morpholinopropanesulfonic acid (MOPS, 147 mg, 704 μmol) in water (5 mL). The majority of the solid dissolved rapidly, but the solution remained turbid even upon dilution to 17 mL. The insoluble material was separated by centrifugation, and the clear supernatant was made basic with 1 M NaOH (1 mL) and stirred for 1 hour at 0° C. The resulting colorless crystalline powder was collected by filtration, washed with cold water containing 1% concentrated aqueous $NH_3$, dried under argon flow followed by vacuum (60° C./0.1 torr), and found to contain no detectable impurities by $^1$H and $^{31}$P NMR. Recovery 160 mg (70%). $^1$H NMR ($CDCl_3$, 400 MHz) δ 1.88 (d, J=12.9 Hz, 12H), 1.96 (d, J=12.9 Hz, 6H), 1.97 (d, J=13.0 Hz, 6H), 2.73-2.79 (m, 2H), 2.82-2.88 (m, 2H), 2.96 (t, J=5.8 Hz, 2H), 3.02-3.11 (m, 4H), 3.51 (dd, J=5.8, 5.6 Hz, 2H), 7.16 (t, J=5.6 Hz, 1H), 7.68 (dt, J=8.0, 3.9 Hz, 1H), 7.80 (dd, J=8.0, 1.7 Hz, 1H), 8.17 (dt, J=3.8, 1.7 Hz, 1H). $^{31}$P NMR ($CDCl_3$, 162 MHz) δ −54.3-−49.3 (m, 2P), 36.5-37.2 (m, 4P). ESI-HRMS calcd for $[M+H]^+$ $C_{21}H_{43}N_2OP_6S_4$ 653.0678, found 653.0665.

N-(2-Acetaminoethyl)-3,4-bis(bis(dimethylphosphorothioylmethyl)phosphino)benzamide (9). Amine derivative 8 (73.7 mg, 113 μmol) was dissolved in DCM (4 mL) and acetic anhydride (43 μL, 4 equiv.) was added. The mixture was stirred for 1 hour, quenched with 5% aqueous NaOH (1 mL), stirred for 10 min, and allowed to settle. The organic layer was collected, and the aqueous layer was extracted with DCM (2×2 mL). The combined organic layers were passed through a plug of $Na_2SO_4$ in a Pasteur pipette and concentrated to give a yellow glassy solid. This was taken up in methanol, treated with activated carbon, filtered, concentrated to dryness, taken up in hot water under argon, filtered, and allowed to cool under slow stirring. The resulting colorless crystals were collected by filtration and dried under vacuum. Yield 26 mg (37 μmol, 33%). $^1$H NMR ($CDCl_3$, 400 MHz) δ 1.89 (d, J=12.8 Hz, 12H), 1.96 (d, J=12.9 Hz, 6H), 1.97 (d, J=13.0 Hz, 6H), 2.04 (s, 3H), 2.76 (dd, J=13.8, 11 Hz, 2H), 2.89 (J=13.9, 11 Hz, 2H), 3.01-3.12 (m, 4H), 3.51-3.59 (m, 4H), 6.22 (t, J=5.4 Hz, 1H), 7.69 (t, dt, J=8.0, 3.8 Hz, 1H), 7.80 (t, J=4.0 Hz, 1H), 7.87 (dd, J=8.0, 1.7 Hz, 1H), 8.13 (td, J=3.8, 1.7 Hz, 1H). $^{31}$P NMR ($CDCl_3$, 162 MHz) −54.2-−49.6 (m, 2P), 36.6-37.3 (m, 4P). ESI-HRMS calcd for $[M+H]^+$ $C_{23}H_{45}N_2O_2P_6S_4$ 695.0784, found 695.0771.

PhenPS-agarose conjugate (10). Purified phenPS-$NH_2$ 8 (131 mg, 200 μmol), MOPS (84 mg, 400 μmol), and $Me_3PS$ (22 mg, internal standard) were shaken together as dry powders, dissolved in water, and diluted to 10 mL within a 15 mL polypropylene centrifuge tube to yield a ligand stock solution. Commercial aldehyde-functionalized crosslinked agarose beads (GoldBio glyoxal agarose 4BCL, 25 mL bottle, minimum 375 μmol aldehyde groups), were collected in a 60 mL fritted funnel and washed with water (200 mL) under gravity flow. Most of the drained gel was gently scooped into a 50 mL polypropylene centrifuge tube using a plastic spatula, and the remainder was transferred with water to a 20 mL gel filtration column. After the excess water drained under gravity flow, the column was inverted, and argon pressure was applied in reverse to eject the plug of gel into the centrifuge tube. Ligand stock solution (9.38 mL, 188 μmol amine) was added, and the tube contents were mixed by inversion for 5 min. $NaBH_3CN$ (94 mg, 1.5 mmol) in water (2 mL) was added, followed by inversion mixing for 30 min. The tube was vented to relieve pressure and subsequently flushed with argon via a 25-gauge needle inserted through the loosened cap, and the needle hole was resealed with a hot glass rod. The tube contents were mixed overnight for 15 hours and then allowed to settle. An aliquot of the supernatant (630 μL) was mixed with $D_2O$ (70 μL), filtered, and compared by $^{31}$P NMR to an aliquot of the original ligand stock solution (300 μL) diluted with $H_2O$ (330 μL) and $D_2O$ (70 μL). Normalization of the peak integrals to the $Me_3PS$ internal standard revealed 89% consumption of the amine.

The settled gel from the previous step (28 mL) was suspended in 6% w/v aqueous $NaHCO_3$, transferred to a 125 mL Erlenmeyer flask, and diluted to 80 mL with $NaHCO_3$ solution, corresponding to 37 mmol total bicarbonate. A reference aliquot (0.3 mL) was collected in an empty polypropylene spin column. The flask was clamped in an ice bath and the suspension was continuously stirred using a bent glass rod coupled to an overhead mechanical stirrer. Acetic anhydride was added in 3 portions of 378 μL (4 mmol) at 30 min intervals. After a further 30 min, the beads were collected in a 60 mL fritted glass funnel and washed with $H_2O$ (200 mL), transferred to an Erlenmeyer flask, and diluted with water to 90 mL. A freshly prepared solution of $NaBH_4$ (380 mg, 10 mmol) in 1 M aqueous KOH (10 mL) was added under stirring. After 1 hour of stirring at ambient temperature, the beads were collected by filtration and washed with water (400 mL) until basicity could no longer be detected by universal indicator paper. As a trace of alkali remained detectable with phenolphthalein, the beads were further washed with buffer (10 mM MOPS-$K^+$, pH 7.2, 25 mL) followed by water (100 mL). To confirm complete consumption of secondary amine functional groups, the reference aliquot before acetylation and an equal volume of the final product were washed with MOPS buffer, equilibrated with 50 μM tartrazine in water, and washed with 2 mL water under gravity flow. Bright yellow staining was observed in the sample prior to acetylation but absent in the acetylated sample, indicating elimination of cationic functional groups.

Example 9: Cu(I)—Binding Capacity and Metal Ion Selectivity of phenPS-Agarose Materials and Methods Aqueous bicinchoninic acid (BCA) stock solution was prepared by dissolving BCA to a concentration of 30 mM in 35 mM aqueous KOH. In a quartz cuvette with 1 cm pathlength, the BCA solution was diluted into PIPES buffer (10 mM, 0.1 M KCl, pH 7.0) to a final concentration of (500 μM), 100 μL of phenPS-agarose 10 (settled gel volume) were added, and the mixture was titrated with [Cu(I)MCL-2]$PF_6$ (30 mM in water) in 15 μM aliquots until the absorbance at 562 nm of the BCA-Cu(I) complex vanished over background.

Results

Figure 14:
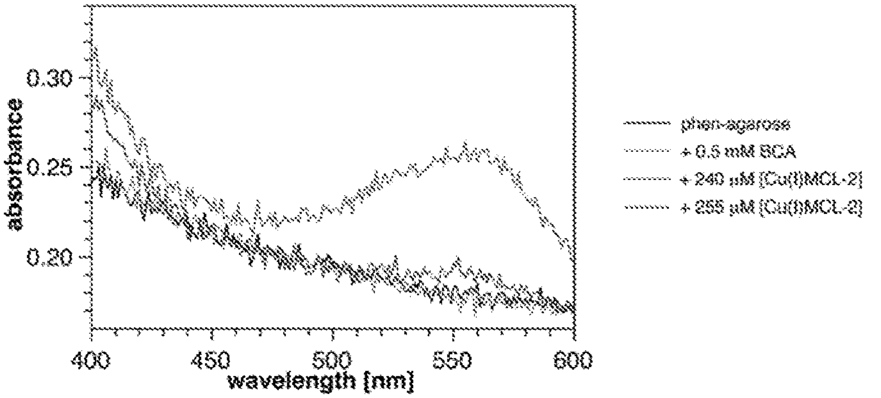
FIG. 14 shows the spectrophotometric determination of the Cu(I) binding capacity of phenPS-agarose (10) using BCA as an indicator. A solution of 10 (50 μM) in the presence of excess BCA (500 μM) was titrated with 15 μM aliquots of Cu(I) (supplied as [Cu(I)MCL-2]) at pH 7.0 (10 mM PIPES, 0.1 M KCl, 25° C.).

FIG. 14 shows that 100 μL phenPS-agarose (settled gel) binds Cu(I) up to a concentration of 240 μM. Further supply of Cu(I) results in the formation of BCA-copper(I) complex as indicated by the increase in absorption at 562 nm. Numeric analysis of the titration data yielded a binding capacity of 4.8 mM Cu(I) for phenPS-agarose 10 (based on settled gel volume).

Example 10: Spectrophotometric Cu(I) Competition Titration of phenPS-NHAc Against BCS Materials and Methods An aqueous sodium bathocuproine disulfonate (BCS, Acros Organics) stock solution (60 mM) was prepared and calibrated by competition titration against MCL-1 as previously described (Bagchi, P., et al., *J. Am. Chem. Soc.,* 135(49) (2013)). BCS (1.50 mM), sodium ascorbate (150 μM) and $CuSO_4$ (30 μM) were sequentially added via aqueous stock solutions to 3 mL of buffer (10 mM PIPES, 0.1 M KCl, pH 7.0, 25° C.) in a 1-cm path length quartz cuvette equipped with magnetic stirring, and a UV-Vis absorption spectrum was recorded from 600-400 nm. PhenPS-NHAc 9 was added in 3 μM aliquots from a 3 mM DMSO stock solution up to a final concentration of 100 μM.

Results

Figures 15A, 15B:
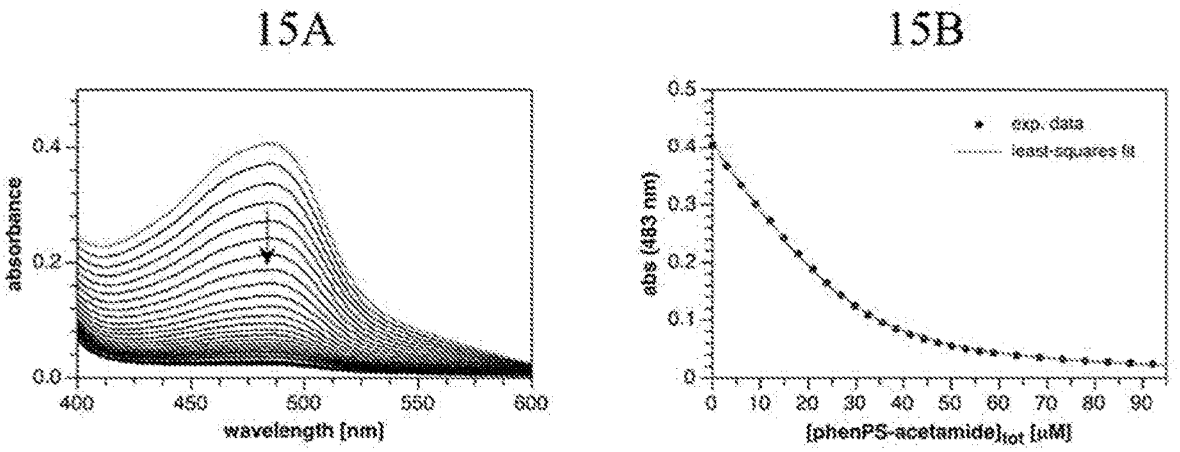
FIG. 15 shows the spectrophotometric determination of the Cu(I) binding affinities of phenPS-NHAc (9) in pH 7.0 buffer (10 mM PIPES, 0.1 M KCl, 25° C.). 15A shows the competition titration of Cu(I) (30 μM, produced by in situ reduction with sodium ascorbate) with phenPS-NHAc in the presence of 1.5 mM BCS. 15B represents the change of absorbance at 483 nm for the titration in plot 15A and non-linear least-squares fit based on the spectral data from 400-650 nm.

Spectrophotometric titration of 30 μM Cu(I) with phenPS-NHAc (9) in the presence of excess BCS resulted in a gradual decrease of the absorption band centered at 483 nm, as shown in FIG. 15. The data were analyzed by nonlinear least-squares fitting over the spectral range from 400 to 600 nm using a 1:1 equilibrium model to yield a stability constant of log $K_{Cu(I)}$=20.60±0.03.

Example 11: Selective Removal of Copper in DMEM Using phenPS-Agarose

Materials and Methods

In Dulbecco's Modification of Eagle's Medium (DMEM), which was supplemented with 10% bovine calf serum (BCS) and 1% penicillin/streptomycin antibiotic solution, 50 μM of aqueous $MnSO_4$, $CoCl_2$, $NiSO_4$, $CuSO_4$, $ZnSO_4$, $(NH)_2Fe(SO_4)_2$ (from a 100 mM aqueous $HClO_4$ stock solution), and RbCl were added. In 500 μL of this solution, 100 μL of the copper sponge slurry was added. The solution was mixed at 4° C. for an hour and centrifuged for 10 min at room temperature. The solution was then diluted by adding 100 μL of ethanol and 800 μL of $dH_2O$ to 100 μL of the mixture and analyzed by TXRF using a Bruker S2 PICOFOX spectrometer using rubidium as an internal standard.

Results

Figure 16:
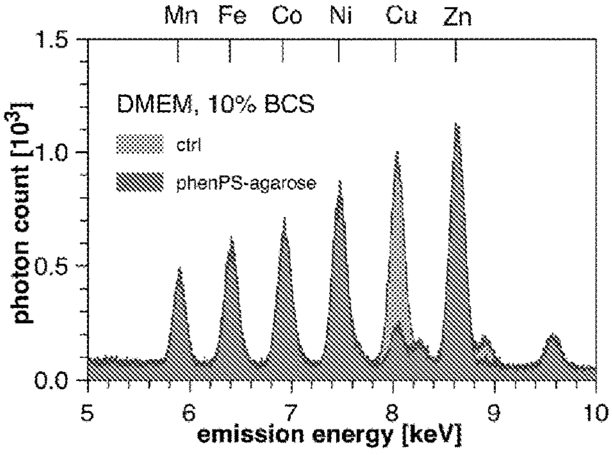
FIG. 16 shows the TXRF elemental analysis of DMEM supplemented with Mn(II), Co(II), Ni(II), Cu(II), Zn(II), and Fe(II) (50 μM each) followed by incubation with phenPS-agarose slurry for 1 hour at 4° C. (green trace) compared to untreated control (blue trace).

Incubation of DMEM/10% BCS containing equimolar amounts of Mn(II), Co(II), Ni(II), Cu(II), Zn(II), and Fe(II) with phenPS-agarose 10 slurry resulted in selective removal of copper as demonstrated with the x-ray fluorescence emission spectrum shown in FIG. 16.

Example 12: Selective Removal of Copper from Cell Lysate Using phenPS-Agarose Materials and Methods Mouse fibroblast cells (3T3) were seeded in 10 cm diameter plates and grown to 90% confluency either in Dulbecco's Modification of Eagle's Medium (DMEM), which was supplemented with 10% FBS, 1% penicillin/streptomycin antibiotic solution, and 50 μM $CuCl_2$. From these plates, the cells were seeded in six 25 cm diameter plates with the same media and grown to confluency. The cells were grown for a total of 13 days with 50 μM $CuCl_2$ at 37° C. under an atmosphere of humidified air containing 5% $CO_2$. The cells were then harvested using a cell scraper and transferred to centrifuge tubes. Cells were pelleted by centrifugation at 180 G at 4° C. for 5 min and washed with cold PBS twice. Cells were then lysed by sonication and pellet by centrifugation at 45,000 G at 4° C. for 30 min. A BCA protein assay was done on the supernatant to give a concentration of 10.2 mg/mL. The supernatant was stored at −80° C.

The analysis of copper removal by the copper sponge was done by adding 100 μL of the phenPS-agarose 10 slurry to 500 μL of the supernatant supplemented with 50 μM aqueous RbCl as an internal standard. In an identical solution, 0.4 mM of PSP-2 from a 3 mM DMSO stock solution was added. The solutions were mixed for at 4° C. for 12 hours, centrifuged for 10 min at room temperature, and analyzed by TXRF using a Bruker S2 PICOFOX spectrometer.

Results

Figure 17:
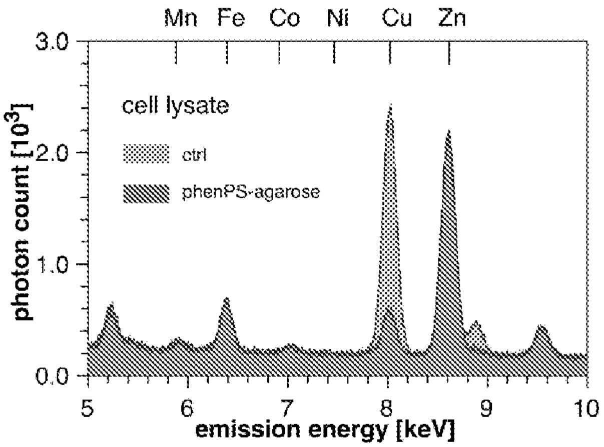
FIG. 17 shows the TXRF elemental analysis of cell lysate from 3T3 mouse fibroblasts that was treated with phenPS-agarose slurry for 12 hours at 4° C. (green trace) compared to untreated control (blue trace).

Incubation of cell lysate from 3T3 mouse fibroblasts with phenPS-agarose slurry resulted in selective removal of copper as demonstrated with the x-ray fluorescence emission spectrum shown in FIG. 17.

Example 13: Synthesis of Crisp-17 (Formula VII)

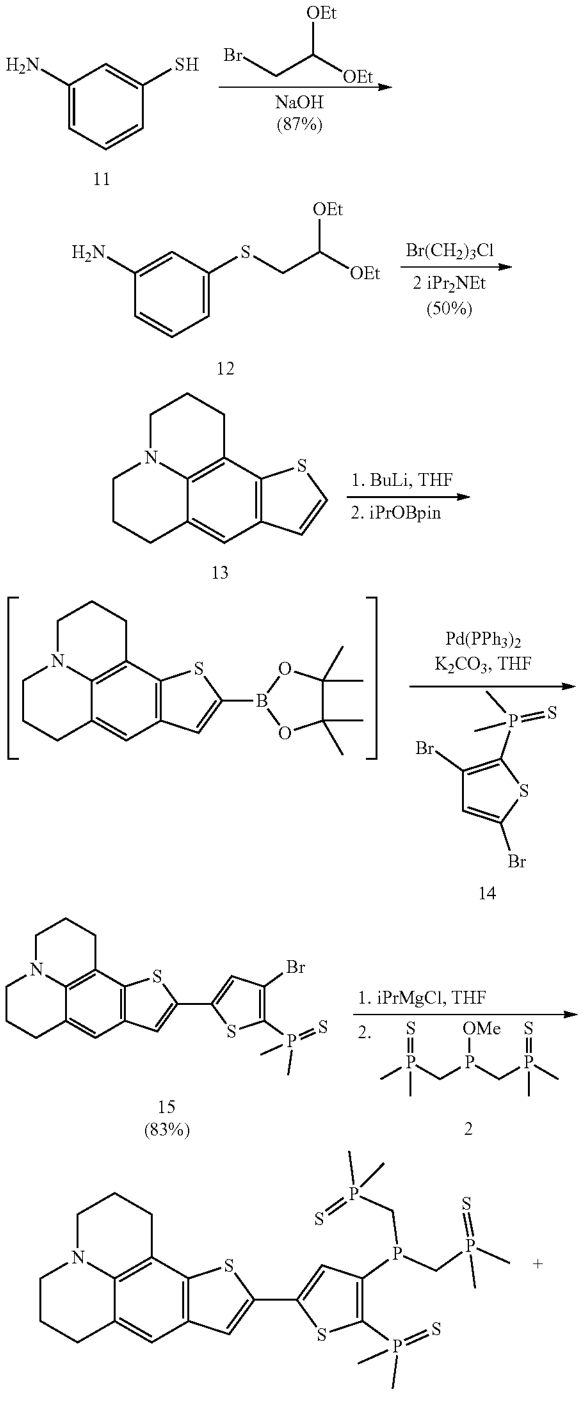

crisp-17
(13%)

-continued

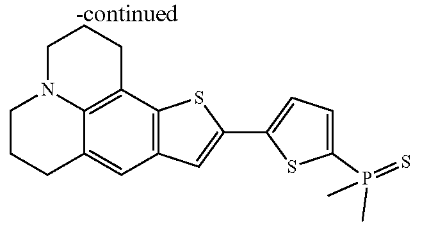

crisp-17ctrl
(60%)

Materials and Methods 3-((2,2-Diethoxyethyl)thio)aniline (12): A 100 mL 2-necked flask containing a stir bar was connected to an argon inlet via the side neck, and 3-aminothiophenol 11 (5.13 g, 41.0 mmol) was added through the top neck against a gentle flow of argon. Ethanol (25 mL, deoxygenated by bubbling with argon) was added, followed by NaOH pellets (1.97 g, 1.2 equiv.) and the flask was sealed with a rubber septum vented to a bubbler. Bromoacetaldehyde diethyl acetal (7.4 mL, 1.2 equiv.) was added by syringe, and the mixture was stirred overnight at room temperature. As a TLC (silica gel, 1:2 hexane-$CH_2Cl_2$) indicated incomplete consumption of 3-aminothiophenol, the septum was replaced with a reflux condenser connected to an argon line and bubbler via a T-adapter, and the mixture was heated to reflux for 1 hour. After cooling, the mixture was partitioned between toluene (150 mL) and water (60 mL). The organic layer was washed with a further 60 mL of water, dried with $Na_2SO_4$, and concentrated. The residue was purified by column chromatography (hexane-MTBE gradient) to give the product 12 as a pale, yellow oil. Yield 8.62 g (35.7 mmol, 87%). $^1$H NMR ($CDCl_3$) δ 1.21 (t, J=7.1 Hz, 6H), 3.11 (d, J=5.6 Hz, 2H), 3.55 (dq, J=9.3 7.1 Hz, 2H), 3.66 (br. s, 2H), 3.67 (dq, J=9.3, 7.1 Hz, 2H), 4.65 (t, J 5.6 Hz, 1H), 6.49 (ddd, J=8.0, 2.3, 0.9 Hz, 1H), 6.70 (dd, J=2.2, 1.8 Hz, 1H), 6.75 (ddd, J=7.7, 1.8, 0.9 Hz, 1H), 7.05 (dd, J=8.0, 7.8 Hz, 1H). $^{13}$C NMR ($CDCl_3$) δ 15.2, 37.0, 62.1, 101.6, 112.9, 115.3, 119.0, 129.6, 137.2, 146.8. EI-MS m/z 241 ($M^+$, 40), 196 (15), 150 (50), 103 (100), 75 (70). EI-HRMS calcd for $M^+$ $C_{12}H_{19}NO_2S$ 241.1131, found 241.1133. 2,3,6,7-Tetrahydro-1H,5H-pyrido[3,2,1-ij]thieno[2,3-f]quinolone (13): A mixture of acetal 12 (2.00 g, 8.29 mmol), N,N-diisopropylethylamine (2.9 mL, 2.0 equiv.) and 1-bromo-3-chloropropane (10 mL, 12 equiv.) was heated to reflux under argon. The initially yellow solution abruptly turned black after 1 hour. After 20 hours a precipitate had formed, and the mixture was allowed to cool. The resulting gray paste was transferred to an Erlenmeyer flask using methanol (25 mL), diluted with water (100 mL), made basic with NaOH, and stirred vigorously with cyclohexane (200 mL) until the mixture readily separated into two clear liquid layers with a thin boundary of tarry material. The cyclohexane layer was separated, dried with $Na_2SO_4$, and concentrated. The product 13 was isolated by column chromatography (hexane-MTBE) and further purified by recrystallization from methanol to give colorless crystals, which quickly turned brown upon storage in air. Yield 863 mg (3.76 mmol, 45%). $^1$H NMR ($CDCl_3$) δ 1.99-2.05 (m, 2H), 2.08-2.14 (m, 2H), 2.85 (t, J=6.7 Hz, 2H), 2.90 (t, J=6.6 Hz, 2H), 3.15-3.19 (m, 4H), 7.05 (d, J=5.4 Hz, 1H), 7.11 (d, J=5.4 Hz, 1H), 7.27 (unresolved coupling, 1H). $^{13}$C NMR ($CDCl_3$) δ 21.8, 22.3, 26.1, 28.2, 50.2, 50.5, 113.4, 120.9, 121.1, 121.3, 123.8, 129.9, 138.9, 140.4. EI-MS m/z 229 ($M^+$, 100), 228 (90), 200 (35). EI-HRMS calcd for $M^+$ $C_{14}H_{15}NS$ 229.0920, found 229.0919. The mother liquor was concentrated to dryness and taken up in 9:1 diethyl ether-ethanol. Chlorotrimethylsilane was added dropwise under stirring, and the resulting precipitate was recrystallized from methanol-isopropanol to give the hydrochloride salt as a cream-colored, air-stable crystalline powder. Yield 105 mg (395 μmol, 5%). Mp 191-193° C. A portion of the HCl salt was converted to the free base by partitioning between 5% NaOH and $CDCl_3$ and verified as the pure product by $^1H$ NMR. Total yield 4.15 mmol (50%).

(3,5-Dibromothiophen-2-yl)dimethylphosphine sulfide (14): A solution of 2,3,5-tribromothiophene (7.15 g, 22.3 mmol) in $Et_2O$ (50 mL) was cooled to −78° C. under argon. A solution of n-BuLi in hexanes (2.5 M, 8.9 mL, 1 molar equiv.) was added dropwise under stirring. After 15 min, diethyl chlorophosphite (3.2 mL, 1 equiv.) was added, and the cooling bath was removed. After warming to room temperature, the mixture was diluted with toluene (100 mL) containing triethylamine (1.5 mL), filtered through a short plug of basic alumina, and concentrated under reduced pressure to give the phosphonite intermediate as a light brown oil, which was used without further purification. $^1H$ and $^{31}P$ NMR in $CDCl_3$ were consistent with a 7:2 mixture of the desired diethyl (3,5-dibromothiophene-2-yl)phosphonite ($^{31}P$ δ 141.8 ppm, $J_{P-C-C-C-H}$=1.6 Hz) and the undesired 4,5-dibromo isomer ($^{31}P$ δ 142.6 ppm, $J_{P-C-C-H}$=3.1 Hz). The intermediate was transferred with toluene (25 mL) to a 2-necked flask containing a stir bar, and the flask was flushed with argon and sealed with a rubber septum vented to a bubbler. A solution of methylmagnesium bromide in $Et_2O$ (3 M, 19 mL, 2.5 equiv.) was added, and the mixture was heated in a 40° C. bath for 2 hours. The resulting slurry was cooled in an ice bath and carefully quenched by dropwise addition of ethanol (2 mL) followed by a solution of citric acid (4.3 g, 1 equiv.) in water (25 mL) under stirring. The septum was removed, and crystalline sulfur (786 mg, 1.1 equiv.) was added against a gentle back-flow of argon. After 30 min, the mixture was partitioned between toluene and water, and the organic layer was dried with $Na_2SO_4$ and concentrated. The residue was separated by column chromatography (hexane-MTBE) to give the product 14 as a light, yellow oil, which solidified on standing. Yield 3.75 g (50%). $^1H$ NMR δ 2.16 (d, J=13.7 Hz, 6H), 7.12 (d, J=1.8 Hz, 1H). $^{31}P\{^1H\}$ NMR ($CDCl_3$) δ 28.9 (s). EI-MS m/z 336 (40), 334 (80), 332 ($M^+$, 40), 321 (15), 319 (30), 317 (15), 255 (100), 253 (95). EI-HRMS calcd for $M^+$ $C_6H_7S_2Br_2P$ 331.8088, found 331.8087.

(3-Bromo-5-(2,3,6,7-tetrahydro-1H,5H-pyrido[3,2,1-ij]thieno[2,3-f]quinolin-10-yl)thiophen-2-yl)dimethylphosphine sulfide (15): Thienojulolidine 13 (352 mg, 1.54 mmol) was dissolved in dry THE (5 mL) under argon. Diisopropylamine (43 μL, 0.2 equiv.) was added, and the mixture was cooled to −78° C. A solution of n-BuLi in hexanes (737 μL, 1.2 equiv.) was added dropwise, and a yellow precipitate slowly formed. The mixture was warmed briefly to 0° C. before cooling back to −78° C., and 2-isopropoxy-4,4,5,5-tetramethyl-1,3,2-dioxaborolane (376 μL, 1.2 equiv.) was added. After warming to room temperature, the resulting homogeneous solution was quenched with 1 M aqueous disodium citrate (1.8 mL, 1.2 equiv.) and quickly diluted with toluene (15 mL) under stirring. The aqueous layer was allowed to settle, removed with a pipette, and extracted with an equal volume of toluene. The combined organic layers were filtered through a plug of $Na_2SO_4$ and concentrated into a 25 mL rb flask. Dibromide 14 (508 mg, 1.54 mmol), $Pd(PPh_3)_4$ (44 mg, 2.5 mol %), $K_2CO_3$ (630 mg, 3 equiv.) THE (8 mL) and water (6 mL) were added, and the mixture was refluxed under argon for 15 hours. The mixture was partitioned between toluene and water, and the organic layer was collected, dried with $Na_2SO_4$, and concentrated. The residue was purified by column chromatography using a gradient of increasing MTBE in 3:1 hexane-$CH_2Cl_2$ followed by crystallization from boiling $CH_2Cl_2$-MTBE to give compound 15 as orange crystalline powder. Yield 610 mg (1.26 mmol, 83%). Mp>200° C. (dec). $^1H$ NMR ($CDCl_3$) δ 1.97-2.03 (m, 2H), 2.07-2.13 (m, 2H), 2.19 (d J=13.7 Hz, 6H), 2.79 (t, J=6.6 Hz, 2H), 2.86 (t, J=6.4 Hz, 2H), 3.19-3.23 (m, 4H), 7.17 (d, J=1.8 Hz, 1H), 7.20 (unresolved coupling, 1H), 7.30 (s, 1H). $^{31}P\{^1H\}$ NMR ($CDCl_3$) S 28.8 (s). EI-MS m/z 483 (100), 481 ($M^+$, 90), 422 (35), 420 (30), 61 (35). EI-HRMS calcd for $M^+$ $C_{20}H_{21}NPS_3Br$ 480.9752, found 480.9742.

(((2-(Dimethylphosphorothioyl)-5-(2,3,6,7-tetrahydro-1H,5H-pyrido[3,2,1-ij]thieno[2,3-f]quinolin-10-yl)thiophen-3-yl)phosphanediyl)bis(methylene))bis(dimethylphosphine sulfide) (crisp-17) (Formula VII):

A 25 mL two-necked flask equipped with a stopcock-gas inlet adapter and stir bar was charged with bromide 15 (583 mg, 1.2 mmol), sealed with a rubber septum, evacuated, back-filled with argon, and vented through the septum to an oil bubbler. THF (5 mL) was added, followed after 5 min by isopropylmagnesium chloride (2 M in THF, 725 μL, 1.2 equiv). Upon addition of the Grignard reagent, the orange starting material rapidly dissolved, and a yellow crystalline precipitate began to form within 15 min. The argon flow rate was increased to evaporate most of the solvent over 1 hour, leaving a yellow paste. The septum was removed and the solid methoxyphosphine 2 (467 mg, 1.4 equiv.) was added against a current of argon. The septum was replaced, and THE (4 mL) was added. After 30 min the flask was placed in a 45° C. bath. The stopcock-gas inlet adapter was closed, and a very slow current of argon was instead introduced via a 90°-bent needle through the septum to minimize solvent evaporation. After 18 hours, the mixture was allowed to cool, quenched with 1 M aqueous disodium citrate (prepared from trisodium citrate and citric acid, 5 mL), and extracted with $CH_2Cl_2$ (25 mL). The organic layer was dried with $Na_2SO_4$ and concentrated to dryness, and the residue was separated by column chromatography, sequentially eluting a trace of unconsumed 15, crisp-17ctrl, and crisp-17 with 15:15:1, 5:5:1, and 2:2:1 hexane-$CH_2Cl_2$-MTBE. Both products were crystallized by bubbling argon through solutions in $CH_2Cl_2$—$CH_3OH$ at 45° C. followed by cooling. Crisp-17: orange prisms, yield 98.5 mg (152 μmol, 13%). Mp>200° C. (dec). $^1H$ NMR ($CD_2Cl_2$) δ 1.79 (d, J 12.9 Hz, 6H), 1.84 (d, J=12.9 Hz, 6H), 1.95-2.01 (m, 2H), 2.05-2.12 (m, 2H), 2.28 (d, J=13.5 Hz, 6H), 2.57-2.63 (m, 2H), 2.79 (d, J=6.6 Hz, 2H) 2.85 (t, J=6.5 Hz, 2H), 3.11-3.18 (m, 2H), 3.19-3.24 (m, 4H), 7.20 (unresolved coupling, 1H), 7.32 (s, 1H), 7.48 (dd, J=2.1, 1.0 Hz, 1H). $^{31}P\{^1H\}$ NMR ($CD_2Cl_2$) δ −60.6 (dt, J=65.4, 11.5 Hz, 1P), 27.4 (d, J=11.5 Hz, 1P), 35.6 (d, J 65.4 Hz, 2P). ESI-HRMS calcd for $M^+$ $C_{26}H_{37}NP_4S_5$ 647.0475, found 647.0473. Crisp-17ctrl: yellow prisms, Yield 295 mg (730 μmol, 60%). Mp 183-184° C. $^1H$ NMR ($CDCl_3$) δ 1.98-2.04 (m, 2H), 2.05 (d, J=13.4 Hz, 6H), 2.06-2.13 (m, 2H), 2.80 (t, J=6.6 Hz, 2H), 2.87 (t, J=6.5 Hz, 2H), 3.19-3.23 (m, 4H), 7.19 (dd, J=3.8, 1.7 Hz, 2H), 7.20 (unresolved coupling, 1H), 7.27 (s, 1H), 7.50 (dd, J=8.7, 3.8 Hz, 1H). $^{31}P\{^1H\}$ NMR ($CDCl_3$) δ 26.0. EI-MS m/z 403 ($M^+$, 100),342 (25), 69 (30). EI-HRMS calcd for $M^+$ $C_{20}H_{22}NPS_3$ 403.0646, found 403.0645.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A compound defined according to formula (V) as follows:

(Formula I)

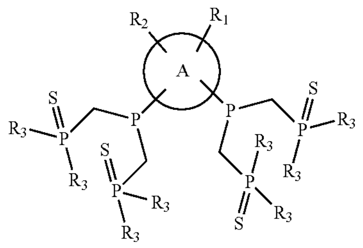

wherein:

A is any 5- or 6-membered aryl or heteroaryl ring;

$R_1$ is —H;

$R_2$ is —COOH, —COO($C_1$-$C_{30}$ alkyl), and —CONH ($C_1$-$C_{30}$ alkyl);

$R_3$ is a —$C_1$-$C_{30}$ alkyl;

or an enantiomer, polymorph or salt thereof.

2. The compound of claim 1, having a structure according to formula (VI) as follows:

(Formula VI)

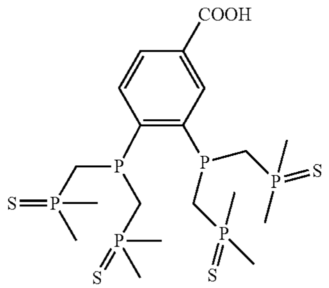

or an enantiomer, polymorph or salt thereof, wherein A is aryl, $R_1$ is H, $R_2$ is —COOH, and $R_3$ is a —$C_1$-$C_{30}$alkyl.

3. The compound of claim 1, further comprising a conjugated small biomolecule.

4. The compound of claim 3, wherein the small biomolecule is biotin.

5. A pharmaceutical composition comprising one or more of the compounds as claimed in claim 1.

6. The pharmaceutical composition of claim 5, further comprising one or more additional active agents.

7. The compound of claim 3 wherein the small biomolecule can be used to conjugate one or more moieties selected from the group consisting of a detection label, protein, or aptamer.

8. The compound of claim 4 wherein the conjugated biotin can be attached to proteins or macromolecules.

* * * * *